(12) United States Patent
Olsen

(10) Patent No.: US 7,659,113 B2
(45) Date of Patent: Feb. 9, 2010

(54) DELIVERY SYSTEM

(75) Inventor: John Christian Olsen, Chapel Hill, NC (US)

(73) Assignee: University of North Carolina at Chapel Hill, Chapel Hill, NC (US)

(*) Notice: Subject to any disclaimer, the term of this patent is extended or adjusted under 35 U.S.C. 154(b) by 30 days.

(21) Appl. No.: 10/910,845

(22) Filed: Aug. 4, 2004

(65) Prior Publication Data

US 2005/0123515 A1 Jun. 9, 2005

Related U.S. Application Data

(63) Continuation-in-part of application No. PCT/GB03/00496, filed on Feb. 4, 2003.

(30) Foreign Application Priority Data

Feb. 4, 2002 (GB) .................................. 0202569

(51) Int. Cl.
*C12N 15/00* (2006.01)
*A61K 48/00* (2006.01)
(52) U.S. Cl. .................................. 435/320.1; 424/93.2
(58) Field of Classification Search .............. 435/320.1; 424/93.2
See application file for complete search history.

(56) References Cited

FOREIGN PATENT DOCUMENTS

WO   WO 99 13905    3/1999
WO   WO 0192508    12/2001

OTHER PUBLICATIONS

Sansom MSP et al. Bioesseay 20:992-1000.*
Stripecke R. Gene Therapy 2000 vol. 96 No. 4 p. 1317-1326.*
Verhoeyen E et al. J Gene Med. Feb. 2004;6 Suppl 1:S83-94.*
Wang G et al. Gene Ther. Jul. 2002;9(14):922-31.*
Delenda C. Lentiviral vectors: optimization of packaging, transduction and gene expression.J Gene Med. 2004.*
Palu et al. Rev Med Virol. May-Jun. 2000;10(3):185-202.*
Lin Ah et al. Virus Res. Feb. 26, 2002;83(1-2):43-56.*
Hatziioannou T et al. J Virol. Jun. 1998;72(6):5313-7.*
Slepushkin VA et la. Mol Ther. Mar. 2001;3(3):395-402.*
Dong et al. J Virol. Dec. 1992;66(12):7374-82.*

Sansom MSP et al. Bioessay 20:992-1000.*
Kobinger et al. Filovirus-pseuodotyped eintiviral vector can efficiently and stably trasnduce airway epthelia in vivo (Nature Biotechnology 2001 vol. 19 p. 225-230.*
Zhang et al., The cytoplasmic tails of the influenza virus spike glycoproteins are required for normal genome packaging. Virology. 269 (2): 325-34, 2000.*
Hatziioannou Theodora et al: "Retroviral display of functional binding domains fused to the amino terminus of influenza hemagglutinin" Human Gene Therapy vol. 10, No. 9 Jun. 10, 1999.
Morrison T. et al.: "Retroviral Expressed Hemagglutinin-Neuraminidase Protein Protects Chick A. HA pseudotyping B. VSV-G pseudotyping

DELIVERY SYSTEM

CROSS-REFERENCE TO RELATED APPLICATIONS

This application is a continuation-in-part of International Application No. PCT/GB03/00496, filed on Feb. 4, 2003, published as WO 03/066868 on Aug. 14, 2003, and claiming priority to British Application No. GB 0202569.0, filed on Feb. 4, 2002.

STATEMENT OF GOVERNMENT SUPPORT

This work may have been supported in part by National Institutes of Health Grant HL051818.

All of the foregoing applications, as well as all documents cited in the foregoing applications ("application documents") and all documents cited or referenced in the application documents are incorporated herein by reference. Also, all documents cited in this application ("herein-cited documents") and all documents cited or referenced in herein-cited documents are incorporated herein by reference. In addition, any manufacturer's instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

FIELD OF THE INVENTION

The present invention relates to a delivery system. In particular, the present invention relates to a retroviral vector capable of delivering a nucleotide sequence of interest (hereinafter abbreviated to "NOI")—or even a plurality of NOIs—to a site of interest.

In particular, the present invention relates to a retroviral delivery system in which the viral vector has been pseudotyped with influenza HA alone or in combination with additional influenza proteins.

The present invention also relates to a retroviral vector useful in gene therapy and, suitably, gene therapy of polarised cells.

BACKGROUND OF THE INVENTION

Gene therapy includes any one or more of: the addition, the replacement, the deletion, the supplementation, the manipulation etc. of one or more nucleotide sequences in, for example, one or more targetted sites—such as targetted cells. If the targetted sites are targetted cells, then the cells may be part of a tissue or an organ. General teachings on gene therapy may be found in Molecular Biology (Ed Robert Meyers, Pub VCH, such as pages 556-558).

By way of further example, gene therapy also provides a means by which any one or more of: a nucleotide sequence, such as a gene, can be applied to replace or supplement a defective gene; a pathogenic gene or gene product can be eliminated; a new gene can be added in order, for example, to create a more favourable phenotype; cells can be manipulated at the molecular level to treat cancer (Schmidt-Wolf and Schmidt-Wolf, 1994, Annals of Hematology 69;273-279) or other conditions—such as immune, cardiovascular, neurological, inflammatory or infectious disorders; antigens can be manipulated and/or introduced to elicit an immune response—such as genetic vaccination.

In recent years, retroviruses have been proposed for use in gene therapy. Essentially, retroviruses are RNA viruses with a life cycle different to that of lytic viruses. In this regard, when a retrovirus infects a cell, its genome is converted to a DNA form. In otherwords, a retrovirus is an infectious entity that replicates through a DNA intermediate. More details on retroviral infection etc. are presented later on.

There are many retroviruses and examples include: murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV).

A detailed list of retroviruses may be found in Coffin et al ("Retroviruses" 1997 Cold Spring Harbour Laboratory Press Eds: J M Coffin, S M Hughes, H E Varmus pp 758-763). Details on the genomic structure of some retroviruses may be found in the art. By way of example, details on HIV may be found from the NCBI Genbank (i.e. Genome Accession No. AF033819).

All retroviruses contain three major coding domains, gag, pol, env, which code for essential virion proteins. Nevertheless, retroviruses may be broadly divided into two categories: namely, "simple" and "complex". These categories are distinguishable by the organisation of their genomes. Simple retroviruses usually carry only this elementary information. In contrast, complex retroviruses also code for additional regulatory proteins derived from multiple spliced messages.

Retroviruses may even be further divided into seven groups. Five of these groups represent retroviruses with oncogenic potential. The remaining two groups are the lentiviruses and the spumaviruses. A review of these retroviruses is presented in "Retroviruses" (1997 Cold Spring Harbour Laboratory Press Eds: J M Coffin, S M Hughes, H E Varmus pp 1-25).

All oncogenic members except the human T-cell leukemia virus-bovine leukemia virus (HTLV-BLV) are simple retroviruses. HTLV, BLV and the lentiviruses and spumaviruses are complex. Some of the best studied oncogenic retroviruses are Rous sarcoma virus (RSV), mouse mammary tumour virus (MMTV) and murine leukemia virus (MLV) and the human T-cell leukemia virus (HTLV).

The *lentivirus* group can be split even further into "primate" and "non-primate". Examples of primate lentiviruses include the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiencey virus (FIV), bovine immunodeficiencey virus (BIV) and Jembrane disease virus (JDV).

A critical distinction between the *lentivirus* family and other types of retroviruses is that lentiviruses have the capability to infect both dividing and non-dividing cells (Lewis et al 1992 EMBO. J 11; 3053-3058, Lewis and Emerman 1994 J. Virol. 68: 510-516). In contrast, other retroviruses—such as MLV—are unable to infect non-dividing cells such as those that make up, for example, muscle, brain, retina, lung, skin and liver tissue including epithelial cells.

During the process of infection, a retrovirus initially attaches to a specific cell surface receptor. On entry into the susceptible host cell, the retroviral RNA genome is then copied to DNA by the virally encoded reverse transcriptase which is carried inside the parent virus. This DNA is transported to the host cell nucleus where it subsequently integrates into the host genome. At this stage, it is typically referred to as the provirus. The provirus is stable in the host chromosome during cell division and is transcribed like other cellular proteins. The provirus encodes the proteins and packaging machinery required to make more virus, which can leave the cell by a process sometimes called "budding".

As already indicated, each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral gene. Encapsidation of the retroviral RNAs occurs by virtue of a psi sequence located at the 5' end of the viral genome.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5'end of the RNA. The sizes of the three elements can vary considerably among different retroviruses.

For ease of understanding, a simple, generic diagram (not to scale) of a retroviral genome showing the elementary features of the LTRs, gag, pol and env is presented in FIG. 1. For the viral genome, the site of transcription initiation is at the boundary between U3 and R in the left hand side LTR (as shown in FIG. 1) and the site of poly (A) addition (termination) is at the boundary between R and U5 in the right hand side LTR (as shown in FIG. 1). U3 contains most of the transcriptional control elements of the provirus, which include the promoter and multiple enhancer sequences responsive to cellular and in some cases, viral transcriptional activator proteins. Some retroviruses have any one or more of the following genes that code for proteins that are involved in the regulation of gene expression: tat, rev, tax and rex.

With regard to the structural genes gag, pol and env themselves, gag encodes the internal structural protein of the virus. Gag is proteolytically processed into the mature proteins MA (matrix), CA (capsid), NC (nucleocapsid). The gene pol encodes the reverse transcriptase (RT), which contains both DNA polymerase, and associated RNase H activities and integrase (IN), which mediates replication of the genome. The gene env encodes the surface (SU) glycoprotein and the transmembrane (TM) protein of the virion, which form a complex that interacts specifically with cellular receptor proteins. This interaction leads ultimately to fusion of the viral membrane with the cell membrane.

The envelope glycoprotein complex of retroviruses includes two polypeptides: an external, glycosylated hydrophilic polypeptide (SU) and a membrane-spanning protein (TM). Together, these form an oligomeric "knob" or "knobbed spike" on the surface of a virion. Both polypeptides are encoded by the env gene and are synthesised in the form of a polyprotein precursor that is proteolytically cleaved during its transport to the cell surface. Although uncleaved Env proteins are able to bind to the receptor, the cleavage event itself is necessary to activate the fusion potential of the protein, which is necessary for entry of the virus into the host cell. Typically, both SU and TM proteins are glycosylated at multiple sites. However, in some viruses, exemplified by MLV, TM is not glycosylated.

Although the SU and TM proteins are not always required for the assembly of enveloped virion particles as such, they do play an essential role in the entry process. In this regard, the SU domain binds to a receptor molecule—often a specific receptor molecule—on the target cell. It is believed that this binding event activates the membrane fusion-inducing potential of the TM protein after which the viral and cell membranes fuse. In some viruses, notably MLV, a cleavage event—resulting in the removal of a short portion of the cytoplasmic tail of TM—is thought to play a key role in uncovering the full fusion activity of the protein (Brody et al 1994 J. Virol. 68: 4620-4627, Rein et al 1994 J. Virol. 68: 1773-1781). This cytoplasmic "tail", distal to the membrane-spanning segment of TM remains on the internal side of the viral membrane and it varies considerably in length in different retroviruses.

Thus, the specificity of the SU/receptor interaction can define the host range and tissue tropism of a retrovirus. In some cases, this specificity may restrict the transduction potential of a recombinant retroviral vector. For this reason, many gene therapy experiments have used MLV. A particular MLV that has an envelope protein called 4070A is known as an amphotropic virus, and this can also infect human cells because its envelope protein "docks" with a phosphate transport protein that is conserved between man and mouse. This transporter is ubiquitous and so these viruses are capable of infecting many cell types. In some cases however, it may be beneficial, especially from a safety point of view, to specifically target restricted cells. To this end, several groups have engineered a mouse ecotropic retrovirus, which unlike its amphotropic relative normally only infects mouse cells, to specifically infect particular human cells. Replacement of a fragment of an envelope protein with an erythropoietin segment produced a recombinant retrovirus which then bound specifically to human cells that expressed the erythropoietin receptor on their surface, such as red blood cell precursors (Maulik and Patel 1997 "Molecular Biotechnology: Therapeutic Applications and Strategies" 1997. Wiley-Liss Inc. pp 45.).

Replacement of the env gene with a heterologous env gene is an example of a technique or strategy called pseudotyping. Pseudotyping is not a new phenomenon and examples may be found in WO-A-98/05759, WO-A-98/05754, WO-A-97/17457, WO-A-96/09400, WO-A-91/00047 and Mebatsion et al 1997 Cell 90, 841-847.

Pseudotyping can confer one or more advantages. For example, with the lentiviral vectors, the env gene product of the HIV based vectors would restrict these vectors to infecting only cells that express a protein called CD4. But if the env gene in these vectors has been substituted with env sequences from other RNA viruses, then they may have a broader infectious spectrum (Verma and Somia 1997 Nature 389:239-242). As just described—and by way of example—workers have pseudotyped an HIV based vector with the glycoprotein from VSV (Verma and Somia 1997 ibid). In addition, WO 99/61639 describes the pseudotyping of a retrovirus with a nucleotide sequence coding for a rabies protein.

Also, and by way of example, the relative fragility of the retroviral Env protein may limit the ability to concentrate retroviral vectors—and concentrating the virus may result in a poor viral recovery.

To some extent, this problem may be overcome by substitution of the retroviral Env protein with the more stable VSV-G protein allowing more efficient vector concentration with better yields (Naldini et al 1996. Science 272: 263-267). However, pseudotyping with VSV-G protein may not always be desirable. This is because the VSV-G protein is cytotoxic (Chen et al 1996, Proc. Natl. Acad. Sci. 10057 and references cited therein).

Hence, it is desirable to find other proteins which are non-toxic and which can be used to pseudotype a retroviral vector.

The influenza haemagglutinin (HA) glycoprotein mediates the binding and fusion of influenza virions to target cells. The receptor for HA is sialic acid and the ability to pseudotype retroviruses with influenza HA would be useful for transducing a broad range of cell types. However, although some studies have demonstrated that it is possible to pseudotype retroviruses with influenza HA protein, the gene transfer titres obtained with HA pseudotyping has been relatively low. Accordingly, there is a need for a method of improving titres obtained with HA pseudotyping.

One important set of target cells for gene therapy are the epithelial cells whose transduction with exogenous NOIs is an important goal in the treatment of diseases such as cystic fibrosis and retinopathies. In epithelial cells, the apical side is most accessible to in vivo gene therapy treatments. However, the apical side of polarized epithelia have proved difficult to transduce by other means. Accordingly, there is also a need for gene therapy vectors having the ability to transduce target epithelial cells through the apical side.

SUMMARY OF THE INVENTION

The present invention seeks to overcome at least some of the problems currently associated with pseudotyped retroviruses by providing an improved retroviral delivery system that has been pseudotyped with an influenza HA protein.

A major advantage of using the influenza HA glycoprotein for pseudotyping in comparison to those used in the prior art such as the VSV glycoprotein is the detailed knowledge of its toxicity to man and other animals due to the extensive use of influenza vaccines. In addition, its natural tropism includes tissues of the respiratory tract, including the lung, making it useful for targeting airway epithelial cells.

According to a first aspect of the present invention there is provided retroviral delivery system capable of transducing a target site, wherein the retroviral delivery system comprises a first nucleotide sequence coding for at least a part of an envelope protein; a second nucleotide sequence coding for at least a part of a second protein and one or more other nucleotide sequences derivable from a retrovirus that ensure transduction of the target site by the retroviral delivery system; wherein the first and second nucleotide sequences are heterologous with respect to at least one of the other nucleotide sequences; and wherein the first nucleotide sequence codes for at least a part of an influenza HA protein or a mutant, variant, homologue, derivative or fragment thereof that is capable of recognising the target site.

Preferably said second protein is another influenza protein, more preferably an influenza matrix protein, most preferably an influenza envelope protein such as the M2 protein. Thus, in accordance with a highly preferred embodiment of the present invention, we surprisingly discovered that the efficiency with which an envelope protein from influenza virus, the influenza HA protein, can pseudotype a retroviral vector can be markedly improved by pseudotyping the vector with a second influenza protein, such as the influenza M2 protein, in addition to the HA protein. The influenza HA protein and second influenza protein may be used to pseudotype a wide variety of retroviral vectors. These include not only vectors constructed from murine oncoretroviruses such as MLV, but also vectors constructed from primate lentiviruses such as HIV and from non-primate lentiviruses such as equine infectious anaemia virus (EIAV).

During influenza A virus infection, M2 has been shown to have important roles at two steps in the virus replication cycle. Both these steps involve the regulation of pH and in both steps the ion channel activity of M2 is used to regulate the flux of protons across cellular or viral membranes. First, during virus production, the ion channel activity of M2 is important for maintaining the pH of the trans-golgi network above the pH necessary for the acid-induced activation of the membrane fusion activity of HA. M2 has previously been shown to enhance the targeting of fusion competent HA to the surface of cells in which it is expressed. It is likely that M2 helps augment EIAV vector production in this manner. A second step at which M2 acts is early after infection at the virus uncoating step, after the virus has been taken up into endosomes by receptor-mediated endocytosis. The ion channel activity of M2 is thought to promote virus uncoating by increasing the acidification of the virion interior thereby decreasing the stability of the viral core particle. Although the details of this step are incompletely understood, the net result is an increased movement of the sub-viral core particle to the nucleus of the cell where influenza virus replicates.

The findings of the present invention are highly surprising. In this respect, although a number of proteins have been used to pseudotype retroviruses, the efficiency with which this is achieved has generally been found to be low, resulting in relatively low viral titres. By pseudotyping a retrovirus with influenza HA protein in the presence of a second protein such as an influenza M2 protein, the viral titre may be markedly increased in comparison with pseudotyping with the influenza HA protein alone.

The retroviral delivery system of the present invention can comprise one entity. Alternatively, the retroviral delivery system of the present invention can comprise a plurality of entities which in combination provide the retroviral delivery system of the present invention. Preferably, the retroviral delivery system is a lentiviral vector. Examples of viral delivery systems include, but are not limited to, herpesviruses and adenoviruses as described, for example, in Savard et al 1997, J Virol 71(5): 4111-4117; Feng et al 1997, Nat Biotechnol 15(9): 866-870.

In a preferred embodiment, the retroviral delivery system is selected from EIAV, HIV and MuLV.

The term "derivable" is used in its normal sense as meaning the sequence need not necessarily be obtained from a retrovirus but instead could be derived therefrom. By way of example, the sequence may be prepared synthetically or by use of recombinant DNA techniques.

Suitably, the influenza HA and influenza M2 proteins are derived from the avian influenza virus, fowl plague virus (FPV).

In addition to the influenza HA protein and the second protein present in the envelope of a vector according to the invention, one or more other envelope proteins may also be present. This may include for example a native envelope protein of the retrovirus. The use of a native envelope protein in addition to a pseudotyping protein can be beneficial to the stability and/or function of the envelope. It may even broaden the infectious profile of the vector. The further protein may, for example, also enhance production of a pseudotyped vector from a producer cell.

In one embodiment, the retroviral delivery system in accordance with the first aspect of the invention further comprises neuraminidase (NA).

Neuraminidase is an enzyme expressed in a number of number of organisms including bacteria and viruses. It is a critical protein on the surface membrane of the influenza virus (Layer et al. *Sci Am.* 1999; January:78-87; Colman P, et al. *Curr Top Microbiol Immunol.* 1985;114:177-255). In particular it enables the replicated influenza virus to bud from host cell and helps the virus to pass through mucous between cells in the entire respiratory tract.

Suitably, NA may be incorporated into the retroviral delivery system by incubation of the producer cells with a neuraminidase protein. In another embodiment, NA may be incorporated into the retroviral delivery system by introducing a cDNA encoding NA into the delivery system. In this embodiment, therefore, the retroviral delivery system of the first aspect of the invention further comprises a third nucleotide sequence which encodes a neuraminidase. Suitably, NA may be bacterial neuraminidase. Alternatively, the NA may be derived from influenza virus. Accordingly, in on preferred embodiment, the nucleotide sequence encoding NA may be an influenza cDNA such as, for example, NA cDNA from influenza A/PR/8/34 (H1N1).

According to a second aspect of the present invention there is provided a viral particle obtainable from the retroviral delivery system according to the present invention.

The invention therefore provides in one aspect a retroviral vector particle pseudotyped with an influenza HA protein and a second protein. Preferably the second protein is another influenza protein, such as an influenza matrix protein, preferably an influenza M2 protein.

According to a third aspect of the present invention there is provided a retroviral vector wherein the retroviral vector is the retroviral delivery system according to the first aspect of the present invention or is obtainable therefrom.

In one embodiment, the vector of the present invention is constructed from or is derivable from a *lentivirus*. This has the advantage that the vector may be capable of transducing non-dividing cells and dividing cells. Thus, the preferred retroviral vectors for pseudotyping according to the invention are *lentivirus* vectors such as HIV, FIV or EIAV vectors. These have the advantages noted above. In particular an influenza HA pseudotyped *lentivirus* vector having influenza virus target cell range will be capable of transducing non-dividing cells such as epithelial cell or cells of the central nervous system such as neurons.

In a preferred embodiment, the retroviral vector according to the present invention may be concentrated. In a particularly preferred embodiment, concentration may be effected by centrifugation as described herein, for example.

According to a fourth aspect of the present invention there is provided a cell transduced with a retroviral delivery system according to the present invention, or a viral particle according to the present invention, or a retroviral vector according to the present invention.

According to a fifth aspect of the present invention there is provided a retroviral delivery system according to the present invention, or a viral particle according to the present invention, or a retroviral vector according to the present invention, for use in medicine.

According to a sixth aspect of the present invention there is provided the use of a retroviral delivery system according to the present invention, or a viral particle according to the present invention, or a retroviral vector according to the present invention in the manufacture of a pharmaceutical composition to deliver a NOI to a target site in need of same.

According to a seventh aspect of the present invention there is provided a method comprising contacting a cell with a retroviral delivery system according to the present invention, or a viral particle according to the present invention, or a retroviral vector according to the present invention.

According to an eighth aspect of the present invention there is provided a vector for preparing a retroviral delivery system according to the present invention, or a viral particle according to the present invention, or a retroviral vector according to the present invention, wherein the vector comprises a nucleotide sequence coding for at least a part of the influenza HA protein or a mutant, variant, derivative or fragment thereof and a nucleotide sequence coding for at least a part of a second protein, preferably an influenza M2 protein, or a mutant, derivative, homologue or fragment thereof.

In one embodiment, the vector further comprises a nucleotide sequence coding for a NA protein or a mutant, variant, derivative or fragment thereof.

According to a ninth aspect of the present invention there is provided a plasmid for preparing a retroviral delivery system according to the present invention, or a viral particle according to the present invention, or a retroviral vector according to the present invention, wherein the plasmid comprises a nucleotide sequence, or a combination of nucleotide sequences selected from a nucleotide sequence coding for at least a part of the influenza HA protein or a mutant, variant, derivative or fragment thereof, a nucleotide sequence coding for at least a part of a second protein, preferably an influenza M2 protein, or a mutant, derivative, or fragment thereof and a nucleotide sequence coding for NA or a mutant, variant, derivative or fragment thereof.

According to a tenth aspect of the present invention there is provided a plurality of plasmids, wherein at least one plasmid is a plasmid according to the present invention and wherein at least one other plasmid comprises one or more nucleotide sequences derivable from a retrovirus.

In another aspect, the invention provides a retroviral vector production system comprising a nucleic acid sequence which encodes an influenza HA protein, a second nucleic acid sequence which encodes a second protein, preferably an influenza protein such as an influenza M2 protein, a nucleic acid sequence which encodes a retrovirus vector genome and optionally one or more further nucleic acid sequences which encode packaging components required for the generation of infective retroviral vector particles containing the genome.

According to an eleventh aspect of the present invention there is provided the use of an influenza HA protein and a second protein, preferably an influenza M2 protein, to pseudotype a retrovirus or a retroviral vector or a retroviral particle in order to affect the infectious profile of the retrovirus or the retroviral vector or the retroviral particle.

In one embodiment, there is provided the additional use of NA in combination with HA and a second protein to generate a pseudotyped retrovirus in accordance with the invention.

In another aspect, the invention provides the use of NA to pseudotype a retrovirus or a retroviral vector or a retroviral particle in order to enhance the infectivity of the retrovirus or the retroviral vector or the retroviral particle.

According to a twelfth aspect of the present invention there is provided the use an influenza HA protein and a second protein, preferably an influenza M2 protein, to pseudotype a retrovirus or a retroviral vector or a retroviral particle in order to affect the host range and/or cell tropism of the retrovirus or the retroviral vector or the retroviral particle.

According to a thirteenth aspect of the present invention there is provided a retrovirus or a retroviral vector or a retroviral particle pseudotyped with an influenza HA protein and a second protein, preferably an influenza M2 protein.

According to a fourteenth aspect of the present invention there is provided a retroviral delivery system comprising a heterologous env region, wherein the heterologous env region comprises at least a part of a nucleotide sequence coding for an influenza HA protein and at least a part of a nucleotide sequence coding for a second protein, preferably an influenza M2 protein.

According to a fifteenth aspect of the present invention there is provided a retroviral delivery system comprising a heterologous env region, wherein the heterologous env region comprises a nucleotide sequence coding for an influenza HA protein and a nucleotide sequence coding for a second protein, preferably an influenza M2 protein.

Preferably the first nucleotide sequence codes for all of an influenza HA protein or a mutant, variant, derivative or fragment thereof.

Preferably the second nucleotide sequence codes for all of an influenza M2 protein or a mutant, variant, derivative or fragment thereof.

Preferably at least one of the other nucleotide sequences is derivable from a *lentivirus* or an oncoretrovirus.

Preferably the other nucleotide sequences are derivable from a *lentivirus* or an oncoretrovirus.

Preferably the other nucleotide sequences are derivable from EIAV, HIV or MLV.

Preferably the retroviral delivery system comprises at least one NOI.

Preferably the NOI has a therapeutic effect or codes for a protein that has a therapeutic effect.

Preferably the target site is a cell. Suitably, said cell is a polarised cell such as an epithelial cells. Preferred epithelial cells are epithelial cells of the airways, or respiratory tract, including the trachea and lung. Other suitable epithelial cells are selected from skin cells, gut epithelial, liver epithelial, cells in the eye (including retinal pigment epithelium) and so forth. In one embodiment, the viral vector in accordance with the invention is capable of transducing a polarised cell through its apical surface.

Thus the present invention provides a retroviral vector having a heterologous envelope protein. This retroviral vector is useful in gene therapy.

An important aspect of the present invention is the pseudotyping of a retrovirus, and/or a retroviral vector derivable or based on same, with a nucleotide sequence coding for an influenza HA protein or a mutant, variant, derivative or fragment thereof in the presence of a second nucleotide sequence encoding a second protein, preferably an influenza M2 protein, or a mutant, variant, derivative or fragment thereof. Here, the term pseudotyping means incorporating in at least a part of, or substituting a part of, or replacing all of, an env gene of a viral genome, or of a viral vector, a protein from another virus.

The presence of the second protein, for example the M2 protein enables efficient pseudotyping with the influenza HA protein.

Thus in a further aspect the present invention provides a method of optimising the pseudotyping of a retrovirus or retroviral vector or retroviral particle with an influenza HA protein comprising pseudotyping said retrovirus or retroviral vector or retroviral particle in the presence of a second nucleotide sequence encoding a second protein. Preferably said second protein is an influenza matrix protein, most preferably an influenza M2 protein, or a mutant, variant, derivative or fragment thereof. Preferably, the retrovirus or retroviral vector or retroviral particle is pseudotyped with both the nucleotide sequence encoding the influenza HA protein and the second protein.

In preferred aspects of the invention, the presence of the second nucleotide sequence and/or second protein encoded by said second nucleotide sequence enhances the titre of the retrovirus, retroviral vector or viral particle produced by the target cell pseudotyped with the influenza HA vector, relative to the titre obtained in the absence of the second nucleotide sequence and/or second protein encoded by said second nucleotide sequence. Preferably the titre obtainable in the presence of the second nucleotide sequence and/or second protein is at least 50%, preferably at least 100%, more preferably at least 200%, more preferably at least 500%, more preferably at least 1000%, more preferably at least 1500%, more preferably at least 2000%, more preferably at least 2500%, more preferably at least 2750%, most preferably at least 3000% greater than that obtainable in the absence of said second nucleotide sequence and/or second protein.

In one embodiment of any aspect of the invention, the retroviral delivery system can be further optimised by treatment of the producer cell with NA. In another embodiment, NA cDNA may be introduced into the producer cell in order to increase vector production.

In a further aspect, the invention provides the use of an influenza HA protein and a second protein to alter the target cell range of a retroviral vector, wherein the second protein is heterologous to the retroviral vector. The second protein is preferably an influenza protein, more preferably an influenza M2 protein.

The use of an influenza HA protein and a second protein, for example an influenza M2 protein, according to the invention provides vectors which, in vivo, preferentially transduce targetted cells which an influenza HA protein preferentially infects. The influenza HA protein mediates virus entry by interacting with receptors which carry oligosaccharides with terminal sialic acid residues an thus interacts with receptors on a broad range of cell types. Thus, the use of influenza HA protein and a second protein according to the invention also enables the provision of vectors which transduce a wide variety of cell types in vitro and also in vivo.

Alternatively, the tropism of the pseudotyped vector particles according to the invention may be modified by the use of a mutant influenza HA protein which is modified in the extracellular domain. Alternatively or additionally, influenza HA proteins from laboratory passaged strains of influenza may be used. These can be screened for alterations in tropism.

An example of an influenza HA protein is shown as SEQ ID NO:1. The present invention covers variants, homologues or derivatives of that sequence.

In another aspect of the invention, there is provided a method of generating a viral vector comprising incubating a retroviral delivery system in accordance with the first aspect of the invention in the presence of NA.

In another aspect, the invention provides a method of producing retroviral vector particles having an envelope comprising an influenza HA protein, which method comprises providing a retroviral vector production system as described herein, in a producer cell, subjecting the producer cell to conditions suitable for the expression of vector particle components and the production of vector particles, and harvesting the vector particles from the supernatant.

The present invention also provides a producer cell expressing the vector genome and the producer plasmid(s) capable of producing a retroviral vector system useful in the present invention.

In yet another aspect, the invention provides a method of transducing a target cell with a NOI, which method comprises contacting the cell with a retroviral vector particle as described herein, carrying the NOI, under conditions to allow attachment to and entry of the vector into the cell such that the NOI enters the target cell genome.

In one embodiment, there is provided a method of transducing an epithelial cell through its apical surface comprising the steps of administering to said epithelial cell an HA pseudotyped viral vector in accordance with any aspect of the invention.

In yet another aspect, the invention provides a use of a vector in accordance with any aspect of the invention in a method of gene therapy of an epithelial target cell.

Suitably the target cell is a respiratory tract epithelial cell including a lung epithelial cell, an intestinal epithelial cell including an epithelial cell of the small or large intestine, a skin epithelial cell or a retinal epithelial cell. In a preferred embodiment, the epithelial cell is a diseased cell.

In one embodiment the use further comprises the step of administration of a retroviral vector in accordance with the invention.

Suitably administration is through topical application, inhalation or through intragastric methods such that said retroviral vector is administered directly to a target cell such as an epithelial cell.

In another aspect there is provided a method of treating and/or preventing a disease comprising administering a retroviral delivery system or a retroviral vector in accordance with the invention.

In another aspect there is provided a pharmaceutical composition comprising a retroviral delivery system or a retroviral vector in accordance with the invention.

In yet another aspect, there is provided a use of a retroviral vector in accordance with the invention in the manufacture of a medicament for use in the treatment of a disease.

Suitably said disease is selected from a respiratory tract disease, including cystic fibrosis, cancer, a disease of the small or large intestine, a skin disease and an eye disease.

Thus, in summation, the present invention relates to a retroviral vector having at least two heterologous envelope proteins, in particular an influenza HA protein and a second protein such as an influenza M2 protein. The present invention also relates to a retroviral vector production system for the production of retroviral vectors having an envelope comprising an influenza HA protein, and, a second protein, preferably an influenza M2 protein, as well as to methods of producing the vector and the systems, and to methods involving the use of the vector and the systems.

The present invention also provides a kit for producing a retroviral vector system useful in the first aspect of the invention, comprising
  (i) a viral vector genome which is incapable of encoding one or more proteins which are required to produce a vector particle;
  (ii) one or more producer plasmid(s) capable of encoding the protein which is not encoded by (i); and optionally
  (iii) a cell suitable for conversion into a producer cell.

In a preferred embodiment, the viral vector genome is incapable of encoding the proteins gag, pol and env. Preferably the kit comprises one or more producer plasmids encoding env, gag and pol, for example, one producer plasmid encoding env and one encoding gag-pol. Preferably the gag-pol sequence is codon optimised for use in the particular producer cell (see below).

The present invention will now be described only by way of example, in which reference will be made to the following Figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9 shows the host range of HA and VSV-G pseudotyped EIAV vectors. The SIN-6.1CZW EIAV vector was pseudotyped with influenza HA/M2/NA or VSV-G and used to transduce various cell lines at 30-50% confluency using serially diluted virus stocks. At 48 hours post-infection, the cells were stained with X-Gal and the titre was determined by counting blue foci.

FIG. 15 shows dose-response of VSV-G pseudotyped EIAV gene transfer to mouse trachea. En face images of X-Gal stained tracheas from the experiments shown in FIGS. 12 and 13 and from similar experiments were captured by a camera. The % surface area X-Gal positive was estimated by measuring the area of cells staining X-gal positive compared to the total area of the trachea exposed to the vector using the Metamorph image analysis system.

DETAILED DESCRIPTION OF THE INVENTION

Figure 1:
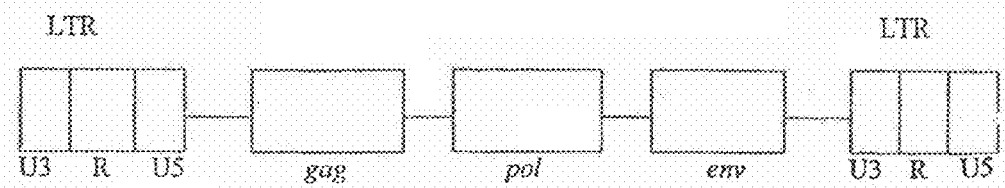
FIG. 1 presents a schematic diagram of a retroviral genome.

Various preferred features and embodiments of the present invention will now be described by way of non-limiting example. Although in general, the techniques mentioned herein are well known in the art, reference may be made in particular to Sambrook, et al., Molecular Cloning, A Laboratory Manual (1989) and Ausubel et al., Short Protocols in Molecular Biology (1999) 4th Ed., John Wiley & Sons, Inc. (as well as the complete version of Current Protocols in Molecular Biology).

As used herein, the term "operably linked" means that the components described are in a relationship permitting them to function in their intended manner.

Mutants, Variants, Homologues, Derivatives

The term "mutant" is used to mean a polypeptide having a primary amino acid sequence which differs from the wild type sequence by one or more amino acid additions, substitutions or deletions. A mutant may arise naturally, or may be created artificially (for example by site-directed mutagenesis). Preferably the mutant has at least 90% sequence identity with the wild type sequence. Preferably the mutant has 20 mutations or less over the whole wild-type sequence. More preferably the mutant has 10 mutations or less, most preferably 5 mutations or less over the whole wild-type sequence.

The term "variant" or "derivative" is used to mean a naturally occurring polypeptide which differs from a wild-type sequence. A variant may be found within the same viral strain (i.e. if there is more than one isoform of the protein) or may be found within different strains. Preferably the variant has at least 90% sequence identity with the wild type sequence. Preferably the variant has 20 mutations or less over the whole wild-type sequence. More preferably the variant has 10 mutations or less, most preferably 5 mutations or less over the whole wild-type sequence. The term "variant" is synonymous with allelic variations of the sequence.

Here, the term "homologue" means an entity having a certain homology with the wild type amino acid sequence and the wild type nucleotide sequence. Here, the term "homology" can be equated with "identity".

In the present context, an homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, an homologous sequence is taken to include a nucleotide sequence which may be at least 75, 85 or 90% identical, preferably at least 95 or 98% identical to the subject sequence. Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ϵ-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid# and L-Phe (4-benzyl)*. The notation* has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

The term "fragment" indicates that the polypeptide comprises a fraction of the wild-type amino acid sequence. It may comprise one or more large contiguous sections of sequence or a plurality of small sections. The polypeptide may also comprise other elements of sequence, for example, it may be a fusion protein with another protein. Preferably the polypeptide comprises at least 50%, more preferably at least 65%, most preferably at least 80% of the wild-type sequence.

With respect to function, the HA mutant, variant, homologue, derivative or fragment should be capable of targetting epithelial cells when used to pseudotype an appropriate vector. In particular, the function is targetting the apical surface of epithelial cells.

With respect to function of the additional influenza envelope protein such as M2 and NA, the mutant, variant, homologue, derivative or fragment should capable of augmenting production of retroviral vectors pseudotyped with HA.

The terms "variant", "homologue" or "fragment" in relation to the amino acid sequence for the preferred HA protein of the present invention include any substitution of, variation of, modification of, replacement of, deletion of or addition of one (or more) amino acid from or to the sequence providing the resultant protein has HA protein activity and/or HA protein characteristics or profile, preferably being at least as biologically active as an HA protein known in the art, for example that disclosed under Genbank accession no 122886 and shown as SEQ ID NO:1. In particular, the term "homologue" covers homology with respect to structure and/or function. With respect to sequence homology, preferably there is at least 75%, more preferably at least 85%, more preferably at least 90% homology to the sequence of an HA protein known in the art, for example that disclosed under Genbank accession no 122886 and shown as SEQ ID NO:1. More preferably there is at least 95%, more preferably at least 98%, homology to the sequence of an HA protein known in the art, for example that disclosed under Genbank accession no 122886 and shown as SEQ ID NO:1. These terms also encompass any one of the at least 13 major antigenic types of HA known.

The terms "variant", "homologue" or "fragment" in relation to the nucleotide sequence coding for the preferred HA protein of the present invention include any substitution of, variation of, modification of, replacement of, deletion of or addition of one (or more) nucleic acid from or to the sequence providing the resultant nucleotide sequence codes for or is capable of coding for a protein having HA protein activity and/or HA protein characteristics or profile, preferably being at least as biologically active as an HA protein known in the art, for example that disclosed under Genbank accession no 122886 and shown as SEQ ID NO:1. In particular, the term "homologue" covers homology with respect to structure and/or function providing the resultant nucleotide sequence codes for or is capable of coding for a protein having HA protein activity and/or HA protein characteristics or profile. With respect to sequence homology, preferably there is at least 75%, more preferably at least 85%, more preferably at least 90% homology to the nucleotide sequence encoding an HA protein known in the art, for example that disclosed under Genbank accession no 122886 and shown as SEQ ID NO:1. More preferably there is at least 95%, more preferably at least 98%, homology to a nucleotide sequence encoding an HA protein known in the art, for example that disclosed under Genbank accession no 122886 and shown as SEQ ID NO:1.

The terms "variant", "homologue" or "fragment" in relation to the amino acid sequence for the preferred second protein of the present invention include any substitution of, variation of, modification of, replacement of, deletion of or addition of one (or more) amino acid from or to the sequence providing the resultant protein has second protein, e.g. M2 protein activity and/or second protein e.g. M2 protein characteristics or profile, preferably being at least as biologically active as an M2 protein known in the art. In particular, the term "homologue" covers homology with respect to structure and/or function. With respect to sequence homology, preferably there is at least 75%, more preferably at least 85%, more preferably at least 90% homology to the sequence of an M2 protein known in the art. More preferably there is at least 95%, more preferably at least 98%, homology to the sequence of an M2 protein known in the art.

The terms "variant", "homologue" or "fragment" in relation to the nucleotide sequence coding for the second protein of the present invention include any substitution of, variation of, modification of, replacement of, deletion of or addition of one (or more) nucleic acid from or to the sequence providing the resultant nucleotide sequence codes for or is capable of coding for a protein having second protein e.g. M2 protein activity and/or second protein e.g. M2 protein characteristics or profile, preferably being at least as biologically active as an M2 protein known in the art. In particular, the term "homologue" covers homology with respect to structure and/or function providing the resultant nucleotide sequence codes for or is capable of coding for a protein having second protein e.g. M2 protein activity and/or second protein e.g. M2 characteristics or profile. With respect to sequence homology, preferably there is at least 75%, more preferably at least 85%, more preferably at least 90% homology to a nucleotide sequence encoding an M2 protein known in the art. More preferably there is at least 95%, more preferably at least 98%, homology to a nucleotide sequence encoding an M2 protein known in the art.

Similarly, the terms "variant", "homologue" or "fragment" in relation to NA incorporate NA derived from bacteria or from any other suitable source. In particular, the term extends to *Vibrio* Cholera derived NA and influenza derived NA, including any one of the, at least, nine major antigenic types.

The term "variant" also encompasses sequences that are complementary to sequences that are capable of hybridising to the nucleotide sequences presented herein. Preferably, the term "variant" encompasses sequences that are complementary to sequences that are capable of hybridising under stringent conditions (e.g. 65° C. and 0.1 SSC {1×SSC=0.15 M NaCl, 0.015 $Na_3$ citrate pH 7.0}) to the nucleotide sequence presented herein.

Vector Delivery Systems and Vector Particles

A vector particle includes the following components: a vector genome, which may contain one or more NOIs, a nucleocapsid encapsidating the nucleic acid, and a membrane surrounding the nucleocapsid.

Suitable vector particles of the present invention are hybrid particles made up of a core lentiviral core particle packaged in a lipid envelope containing influenza envelope proteins. Core particles comprise the nucleocapsid proteins.

The term "nucleocapsid" refers to at least the group specific viral core proteins (gag) and the viral polymerase (pol) of a retrovirus genome. These proteins encapsidate the packagable sequences and are themselves further surrounded by a membrane containing an envelope glycoprotein.

Viral vector or viral delivery systems include but are not limited to adenoviral vectors, adeno-associated viral (AAV) vectors, herpes viral vectors, retroviral vectors, lentiviral vectors, and baculoviral vectors.

The term "vector genome" refers to both to the RNA construct present in the retroviral vector particle and the integrated DNA construct. The term also embraces a separate or isolated DNA construct capable of encoding such an RNA genome. A retroviral or lentiviral genome should comprise at least one component part derivable from a retrovirus or a *lentivirus*. The term "derivable" is used in its normal sense as meaning a nucleotide sequence or a part thereof which need not necessarily be obtained from a virus such as a *lentivirus* but instead could be derived therefrom. By way of example, the sequence may be prepared synthetically or by use of recombinant DNA techniques. Preferably the genome comprises apsi region (or an analogous component which is capable of causing encapsidation).

The viral vector genome is preferably "replication defective" by which we mean that the genome does not comprise sufficient genetic information alone to enable independent replication to produce infectious viral particles within the recipient cell. In a preferred embodiment, the genome lacks a functional env, gag or pol gene. If a highly preferred embodiment the genome lacks env, gag and pol genes.

The viral vector genome may comprise some or all of the long terminal repeats (LTRs). Preferably the genome comprises at least part of the LTRs or an analogous sequence which is capable of mediating proviral integration, and transcription. The sequence may also comprise or act as an enhancer-promoter sequence.

In addition to gag, pol and env, the complex retroviruses also contain "accessory" or "additional" genes which code for accessory or auxillary proteins. Accessory or auxiliary proteins are defined as those proteins encoded by the accessory genes in addition to those encoded by the usual replicative or structural genes, gag, pol and env. These accessory proteins are distinct from those involved in the regulation of gene expression, like those encoded by tat, rev, tax and rex. Examples of accessory genes include one or more of vif, vpr, vpx, vpu and nef. These accessory genes can be found in, for example, HIV (see, for example pages 802 and 803 of "Retroviruses" Ed. Coffin et al Pub. CSHL 1997). EIAV has, amongst others, the additional gene, S2.

Proteins encoded by additional genes serve various functions, some of which may be duplicative of a function provided by a cellular protein. In EIAV, for example, tat acts as a transcriptional activator of the viral LTR. It binds to a stable, stem-loop RNA secondary structure referred to as TAR. Rev regulates and co-ordinates the expression of viral genes through rev-response elements (RRE). The mechanisms of action of these two proteins are thought to be broadly similar to the analogous mechanisms in the primate viruses. The function of S2 is unknown. In addition, an EIAV protein, Ttm, has been identified that is encoded by the first exon of tat spliced to the env coding sequence at the start of the transmembrane protein.

Non-essential accessory proteins may function in specialised cell types, providing functions that are at least in part duplicative of a function provided by a cellular protein. Typically, the accessory genes are located between pol and env, just downstream from env including the U3 region of the LTR or overlapping portions of the env and each other.

The complex retroviruses have evolved regulatory mechanisms that employ virally encoded transcriptional activators as well as cellular transcriptional factors. These trans-acting viral proteins serve as activators of RNA transcription directed by the LTRs. The transcriptional trans-activators of the lentiviruses are encoded by the viral tat genes. Tat binds to a stable, stem-loop, RNA secondary structure, referred to as TAR, one function of which is to apparently optimally position Tat to trans-activate transcription.

As mentioned earlier, retroviruses have been proposed as a delivery system (otherwise expressed as a delivery vehicle or delivery vector) for inter alia the transfer of a NOI, or a plurality of NOIs, to one or more sites of interest. The transfer can occur in vitro, ex vivo, in vivo, or combinations thereof. When used in this fashion, the retroviruses are typically called retroviral vectors or recombinant retroviral vectors. Retroviral vectors have even been exploited to study various aspects of the retrovirus life cycle, including receptor usage, reverse transcription and RNA packaging (reviewed by Miller, 1992 Curr Top Microbiol Immunol 158:1-24).

In a typical recombinant retroviral vector for use in gene therapy, at least part of one or more of the gag, pol and env protein coding regions may be removed from the virus. This makes the retroviral vector replication-defective. The removed portions may even be replaced by a NOI in order to generate a virus capable of integrating its genome into a host genome but wherein the modified viral genome is unable to propagate itself due to a lack of structural proteins. When integrated in the host genome, expression of the NOI occurs—resulting in, for example, a therapeutic effect. Thus, the transfer of a NOI into a site of interest is typically achieved by: integrating the NOI into the recombinant viral vector; packaging the modified viral vector into a virion coat; and allowing transduction of a site of interest—such as a targetted cell or a targetted cell population.

It is possible to propagate and isolate quantities of retroviral vectors (e.g. to prepare suitable titres of the retroviral vector) for subsequent transduction of, for example, a site of interest by using a combination of a packaging or helper cell line and a recombinant vector.

As used herein, the term "packaging cell" refers to a cell which contains those elements necessary for production of infectious recombinant virus which are lacking in the RNA genome. Typically, such packaging cells contain one or more producer plasmids which are capable of expressing viral structural proteins (such as gag-pol and env, which may be codon optimised) but they do not contain a packaging signal.

The term "packaging signal" which is referred to interchangeably as "packaging sequence" or "psi" is used in reference to the non-coding, cis-acting sequence required for encapsidation of retroviral RNA strands during viral particle formation. In HIV-1, this sequence has been mapped to loci extending from upstream of the major splice donor site (SD) to at least the gag start codon.

Packaging cell lines may be readily prepared (see also WO 92/05266), and utilised to create producer cell lines for the production of retroviral vector particles. As already mentioned, a summary of the available packaging lines is presented in "Retroviruses" (as above).

It is known that the separate expression of the components required to produce a retroviral vector particle on separate DNA sequences cointroduced into the same cell will yield retroviral particles carrying defective retroviral genomes that carry therapeutic genes (e.g. Reviewed by Miller 1992). This cell is referred to as the producer cell (see below).

There are two common procedures for generating producer cells. In one, the sequences encoding retroviral Gag, Pol and Env proteins are introduced into the cell and stably integrated into the cell genome; a stable cell line is produced which is referred to as the packaging cell line. The packaging cell line produces the proteins required for packaging retroviral RNA but it cannot bring about encapsidation due to the lack of a psi region. However, when a vector genome (having a psi region) is introduced into the packaging cell line, the helper proteins can package the psi-positive recombinant vector RNA to produce the recombinant virus stock. This can be used to transduce the NOI into recipient cells. The recombinant virus whose genome lacks all genes required to make viral proteins can infect only once and cannot propagate. Hence, the NOI is introduced into the host cell genome without the generation of potentially harmful retrovirus. A summary of the available packaging lines is presented in "Retroviruses" (1997 Cold Spring Harbour Laboratory Press Eds: J M Coffin, S M Hughes, H E Varmus pp 449).

The present invention also provides a packaging cell line comprising a viral vector genome which is capable of producing a vector system useful in the first aspect of the invention. For example, the packaging cell line may be transduced with a viral vector system comprising the genome or transfected with a plasmid carrying a DNA construct capable of encoding the RNA genome. The present invention also provides a kit for producing a retroviral vector system useful in the first aspect of the invention which comprises a packaging cell and a retroviral vector genome.

However, this technique can be problematic in the sense that the titre levels are not always at a satisfactory level. Nevertheless, the design of retroviral packaging cell lines has evolved to address the problem of inter alia the spontaneous production of helper virus that was frequently encountered with early designs. As recombination is greatly facilitated by homology, reducing or eliminating homology between the genomes of the vector and the helper has reduced the problem of helper virus production.

The second approach is to introduce the three different DNA sequences that are required to produce a retroviral vector particle i.e. the env coding sequences, the gag-pol coding sequence and the defective retroviral genome containing one or more NOIs into the cell at the same time by transient transfection and the procedure is referred to as transient triple transfection (Landau & Littman 1992; Pear et al 1993). The triple transfection procedure has been optimised (Soneoka et al 1995; Finer et al 1994). WO 94/29438 describes the production of producer cells in vitro using this multiple DNA transient transfection method. WO 97/27310 describes a set of DNA sequences for creating retroviral producer cells either in vivo or in vitro for re-implantation.

The components of the viral system which are required to complement the vector genome may be present on one or more "producer plasmids" for transfecting into cells.

Transient transfection can also be used to measure vector production when vectors are being developed. Transient transfection has numerous advantages over the packaging cell method. In this regard, transient transfection avoids the longer time required to generate stable vector-producing cell lines and is used if the vector or retroviral packaging components are toxic to cells. Components typically used to generate retroviral vectors include a plasmid encoding the Gag/Pol proteins, a plasmid encoding the Env protein and a plasmid containing a NOI. Vector production involves transient transfection of one or more of these components into cells containing the other required components. If the vector encodes toxic genes or genes that interfere with the replication of the host cell, such as inhibitors of the cell cycle or genes that induce apoptosis, it may be difficult to generate stable vector-producing cell lines, but transient transfection can be used to produce the vector before the cells die. Also, cell lines have been developed using transient infection that produce vector titre levels that are comparable to the levels obtained from stable vector-producing cell lines (Pear et al 1993, PNAS 90:8392-8396).

Self-Inactivating Vector System

Preferably the retroviral vector system used in the first aspect of the present invention is a self-inactivating (SIN) vector system.

By way of example, self-inactivating retroviral vector systems have been constructed by deleting the transcriptional enhancers or the enhancers and promoter in the U3 region of the 3' LTR. After a round of vector reverse transcription and integration, these changes are copied into both the 5' and the 3' LTRs producing a transcriptionally inactive provirus. However, any promoter(s) internal to the LTRs in such vectors will still be transcriptionally active. This strategy has been employed to eliminate effects of the enhancers and promoters in the viral LTRs on transcription from internally placed genes. Such effects include increased transcription or suppression of transcription. This strategy can also be used to eliminate downstream transcription from the 3' LTR into genomic DNA. This is of particular concern in human gene therapy where it may be important to prevent the adventitious activation of an endogenous oncogene.

Recombinase Assisted Mechanism

Preferably a recombinase assisted mechanism is used which facilitates the production of high titre regulated lentiviral vectors from the producer cells of the present invention.

As used herein, the term "recombinase assisted system" includes but is not limited to a system using the Cre recombinase/loxP recognition sites of bacteriophage P1 or the site-specific FLP recombinase of S. cerevisiae which catalyses recombination events between 34 bp FLP recognition targets (FRTs).

The site-specific FLP recombinase of S. cerevisiae which catalyses recombination events between 34 bp FLP recognition targets (FRTs) has been configured into DNA constructs in order to generate high level producer cell lines using recombinase-assisted recombination events (Karreman et al (1996) NAR 24:1616-1624). A similar system has been developed using the Cre recombinase/loxP recognition sites of bacteriophage P1 (see PCT/GB00/03837; Vanin et al (1997) J. Virol 71:7820-7826). This was configured into a lentiviral genome such that high titre lentiviral producer cell lines were generated.

By using producer/packaging cell lines, it is possible to propagate and isolate quantities of retroviral vector particles (e.g. to prepare suitable titres of the retroviral vector particles) for subsequent transduction of, for example, a site of interest (such as an epithelial cell). Producer cell lines are usually better for large scale production of vector particles.

Producer cells/packaging cells can be of any suitable cell type. Producer cells are generally mammalian cells but can be, for example, insect cells.

As used herein, the term "producer cell" or "vector producing cell" refers to a cell which contains all the elements necessary for production of retroviral vector particles.

Preferably, the producer cell is obtainable from a stable producer cell line.

Preferably, the producer cell is obtainable from a derived stable producer cell line.

Preferably, the producer cell is obtainable from a derived producer cell line.

As used herein, the term "derived producer cell line" is a transduced producer cell line which has been screened and selected for high expression of a marker gene. Such cell lines support high level expression from the retroviral genome. The term "derived producer cell line" is used interchangeably with the term "derived stable producer cell line" and the term "stable producer cell line.

Preferably the derived producer cell line includes but is not limited to a retroviral and/or a lentiviral producer cell.

Preferably the derived producer cell line is an HIV or EIAV producer cell line, more preferably an EIAV producer cell line.

Preferably the envelope protein sequences, and nucleocapsid sequences are all stably integrated in the producer and/or packaging cell. However, one or more of these sequences could also exist in episomal form and gene expression could occur from the episome.

Preferably the producer cell is treated with neuraminidase. As described herein, this may be through the introduction of a recombinant or purified protein or through the introduction of a cDNA.

Also as discussed above, simple packaging cell lines, comprising a provirus in which the packaging signal has been deleted, have been found to lead to the rapid production of undesirable replication competent viruses through recombination. In order to improve safety, second generation cell lines have been produced wherein the 3'LTR of the provirus is deleted. In such cells, two recombinations would be necessary to produce a wild type virus. A further improvement involves the introduction of the gag-pol genes and the env gene on separate constructs so-called third generation packaging cell lines. These constructs are introduced sequentially to prevent recombination during transfection.

Preferably, the packaging cell lines are second generation packaging cell lines.

Preferably, the packaging cell lines are third generation packaging cell lines.

In these split-construct, third generation cell lines, a further reduction in recombination may be achieved by changing the codons. This technique, based on the redundancy of the genetic code, aims to reduce homology between the separate constructs, for example between the regions of overlap in the gag-pol and env open reading frames.

The packaging cell lines are useful for providing the gene products necessary to encapsidate and provide a membrane protein for a high titre vector particle production. The packaging cell may be a cell cultured in vitro such as a tissue culture cell line. Suitable cell lines include but are not limited to mammalian cells such as murine fibroblast derived cell lines or human cell lines. Preferably the packaging cell line is a human cell line, such as for example: HEK293, 293-T, TE671, HT1080.

Alternatively, the packaging cell may be a cell derived from the individual to be treated such as a monocyte, macrophage, blood cell or fibroblast. The cell may be isolated from an individual and the packaging and vector components administered ex vivo followed by re-administration of the autologous packaging cells.

It is highly desirable to use high-titre virus preparations in both experimental and practical applications. Techniques for increasing viral titre include using a psi plus packaging signal as discussed above and concentration of viral stocks such as ultracentrifugation, as described herein.

As used herein, the term "high titre" means an effective amount of a retroviral vector or particle which is capable of transducing a target site such as a cell.

As used herein, the term "effective amount" means an amount of a regulated retroviral or lentiviral vector or vector particle which is sufficient to induce expression of the NOIs at a target site.

A high-titre viral preparation for a producer/packaging cell is usually of the order of $10^5$ to $10^7$ t.u. per ml. (The titer is expressed in transducing units per ml (t.u./ml) as titred on a standard D17 cell line). For transduction in tissues such as the brain, it is necessary to use very small volumes, so the viral preparation is concentrated by ultracentrifugation. The resulting preparation should have at least $10^8$ t.u./ml, preferably from $10^8$ to $10^9$ t.u./ml, more preferably at least $10^9$ t.u./ml.

The presence of a sequence termed the central polypurine tract (cPPT) may improve the efficiency of gene delivery to non-dividing cells (see WO 00/31200). This cis-acting element is located, for example, in the EIAV polymerase coding region element. Preferably the genome of the vector system used in the present invention comprises a cPPT sequence.

In addition, or in the alternative, the viral genome may comprise a post-translational regulatory element and/or a translational enhancer.

Minimal Systems

The retroviral vector genomes of the present invention for subsequent use in gene therapy preferably contain the minimum retroviral material necessary to function efficiently as vectors. The purpose of this is to allow space for the incorporation of the NOI(s), and for safety reasons. Retroviral vector genomes are preferably replication defective due to the absence of functional genes encoding one or more of the structural (or packaging) components encoded by the gag-pol and env genes. The absent components required for particle production are provided in trans in the producer cell. The absence of virus structural components in the genome also means that undesirable immune responses generated against virus proteins expressed in the target cell are reduced or avoided. Furthermore, possible reconstruction of infectious viral particles is preferably avoided where in vivo use is contemplated. Therefore, the viral structural components are preferably excluded from the genome as far as possible, in order to reduce the chance of any successful recombination.

It has been demonstrated that a primate *lentivirus* minimal system can be constructed which requires none of the HIV/SIV additional genes vif, vpr, vpx, vpu, tat, rev and nef for either vector production or for transduction of dividing and non-dividing cells. It has also been demonstrated that an EIAV minimal vector system can be constructed which does not require S2 for either vector production or for transduction of dividing and non-dividing cells. The deletion of additional genes is highly advantageous. Firstly, it permits vectors to be produced without the genes associated with disease in lentiviral (e.g. HIV) infections. In particular, tat is associated with disease. Secondly, the deletion of additional genes permits the vector to package more heterologous DNA. Thirdly, genes whose function is unknown, such as S2, may be omitted, thus reducing the risk of causing undesired effects. Examples of minimal lentiviral vectors are disclosed in WO-A-99/32646 and in WO-A-98/17815.

Thus, preferably, the delivery system used in the invention is devoid of at least tat and S2 (if it is an EIAV vector system), and possibly also vif, vpr, vpx, vpu and nef. More preferably, the systems of the present invention are also devoid of rev. Rev was previously thought to be essential in some retroviral genomes for efficient virus production. For example, in the case of HIV, it was thought that rev and RRE sequence should be included. However, it has been found that the requirement for rev and RRE can be reduced or eliminated by codon optimisation (see below) or by replacement with other functional equivalent systems such as the MPMV system. As expression of the codon optimised gag-pol is REV independent, RRE can be removed from the gag-pol expression cassette, thus removing any potential for recombination with any RRE contained on the vector genome.

In a preferred embodiment the viral genome of the first aspect of the invention lacks the Rev response element (RRE).

In a preferred embodiment, the system used in the present invention is based on a so-called "minimal" system in which some or all of the additional genes have be removed.

Codon Optimisation

Codon optimisation has previously been described in WO99/41397. Different cells differ it their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. By the same token, it is possible to decrease expression by deliberately choosing codons for which the corresponding tRNAs are known to be rare in the particular cell type. Thus, an additional degree of translational control is available.

Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms.

Codon optimisation has a number of other advantages. By virtue of alterations in their sequences, the nucleotide sequences encoding the packaging components of the viral particles required for assembly of viral particles in the producer cells/packaging cells have RNA instability sequences (INS) eliminated from them. At the same time, the amino acid sequence coding sequence for the packaging components is retained so that the viral components encoded by the sequences remain the same, or at least sufficiently similar that the function of the packaging components is not compromised. Codon optimisation also overcomes the Rev/RRE requirement for export, rendering optimised sequences Rev independent. Codon optimisation also reduces homologous recombination between different constructs within the vector system (for example between the regions of overlap in the gag-pol and env open reading frames). The overall effect of codon optimisation is therefore a notable increase in viral titre and improved safety.

In one embodiment only codons relating to INS are codon optimised. However, in a much more preferred and practical embodiment, the sequences are codon optimised in their entirety, with the exception of the sequence encompassing the frameshift site.

The gag-pol gene comprises two overlapping reading frames encoding the gag-pol proteins. The expression of both proteins depends on a frameshift during translation. This frameshift occurs as a result of ribosome "slippage" during translation. This slippage is thought to be caused at least in part by ribosome-stalling RNA secondary structures. Such secondary structures exist downstream of the frameshift site in the gag-pol gene. For HIV, the region of overlap extends from nucleotide 1222 downstream of the beginning of gag (wherein nucleotide 1 is the A of the gag ATG) to the end of gag (nt 1503). Consequently, a 281 bp fragment spanning the frameshift site and the overlapping region of the two reading frames is preferably not codon optimised. Retaining this fragment will enable more efficient expression of the gag-pol proteins.

For EIAV the beginning of the overlap has been taken to be nt 1262 (where nucleotide 1 is the A of the gag ATG). The end of the overlap is at 1461 bp. In order to ensure that the frameshift site and the gag-pol overlap are preserved, the wild type sequence has been retained from nt 1156 to 1465.

Derivations from optimal codon usage may be made, for example, in order to accommodate convenient restriction sites, and conservative amino acid changes may be introduced into the gag-pol proteins.

In a highly preferred embodiment, codon optimisation was based on lightly expressed mammalian genes. The third and sometimes the second and third base may be changed.

Due to the degenerate nature of the Genetic Code, it will be appreciated that numerous gag-pol sequences can be achieved by a skilled worker. Also there are many retroviral variants described which can be used as a starting point for generating a codon optimised gag-pol sequence. Lentiviral genomes can be quite variable. For example there are many quasi-species of HIV-1 which are still functional. This is also the case for EIAV. These variants may be used to enhance particular parts of the transduction process. By way of example, details on HIV and EIAV may be found from the NCBI Genbank database maintained by the National Institutes of Health. Details of HIV variants may also be found in the HIV databases maintained by Los Alamos National Laboratory.

The strategy for codon optimised gag-pol sequences can be used in relation to any retrovirus. This would apply to all lentiviruses, including EIAV, FIV, BIV, CAEV, VMR, SIV, HIV-1 and HIV-2. In addition this method could be used to increase expression of genes from HTLV-1, HTLV-2, HFV, HSRV and human endogenous retroviruses (HERV), MLV and other retroviruses.

Codon optimisation can render gag-pol expression Rev independent. In order to enable the use of anti-rev or RRE factors in the retroviral vector, however, it would be necessary to render the viral vector generation system totally Rev/RRE independent. Thus, the genome also needs to be modified. This is achieved by optimising vector genome components. Advantageously, these modifications also lead to the production of a safer system absent of all additional proteins both in the producer and in the transduced cell.

As described above, the packaging components for a retroviral vector include expression products of gag, pol and env genes. In addition, efficient packaging depends on a short sequence of 4 stem loops followed by a partial sequence from gag and env (the "packaging signal"). Thus, inclusion of a deleted gag sequence in the retroviral vector genome (in addition to the full gag sequence on the packaging construct) will optimise vector titre. To date efficient packaging has been reported to require from 255 to 360 nucleotides of gag in vectors that still retain env sequences, or about 40 nucleotides of gag in a particular combination of splice donor mutation, gag and env deletions. It has surprisingly been found that a deletion of all but the N-terminal 360 or so nucleotides in gag leads to an increase in vector titre. Thus, preferably, the retroviral vector genome includes a gag sequence which comprises one or more deletions, more preferably the gag sequence comprises about 360 nucleotides derivable from the N-terminus.

Once within the cell, the RNA genome from a retroviral vector particle is reverse transcribed into DNA and integrated into the DNA of the recipient cell.

As used herein the term "vector system" also includes a vector particle capable of transducing a recipient cell with an NOI.

The retroviral delivery system and vectors of the present invention are useful for the delivery of one or more NOIs to cells in vivo and in vitro, in particular the delivery of therapeutically active NOI(s). One or more selected NOI(s) may be incorporated in the vector genome for expression in the target cell. The NOI(s) may have one or more expression control sequences of their own, or their expression may be controlled by the vector LTRs. For appropriate expression of the NOI(s), a promoter may be included in or between the LTRs which is preferentially active under certain conditions or in certain cell types. The NOI may be a sense sequence or an antisense sequence. Furthermore, if there is a plurality of NOIs then those NOIs may be sense sequences or antisense sequences or combinations thereof.

The retroviral vector genome of the present invention may generally comprise LTRs at the 5' and 3' ends, one or more NOI(s) including therapeutically active genes and/or marker genes, or suitable insertion sites for inserting one or more NOI(s), and a packaging signal to enable the genome to be packaged into a vector particle in a producer cell. There may even be suitable primer binding sites and integration sites to allow reverse transcription of the vector RNA to DNA, and integration of the proviral DNA into the target cell genome. In a preferred embodiment, the retroviral vector particle has a reverse transcription system (compatible reverse transcription and primer binding sites) and an integration system (compatible integrase and integration sites).

Thus, in accordance with the present invention, it is possible to manipulate the viral genome or the retroviral vector nucleotide sequence, so that viral genes are replaced or supplemented with one or more NOIs. The NOI(s) may be any one or more of selection gene(s), marker gene(s) and therapeutic gene(s). Many different selectable markers have been used successfully in retroviral vectors. These are reviewed in "Retroviruses" (1997 Cold Spring Harbour Laboratory Press Eds: J M Coffin, S M Hughes, H E Varmus pp 444) and include, but are not limited to, the bacterial neomycin and hygromycin phosphotransferase genes which confer resistance to G418 and hygromycin respectively; a mutant mouse dihydrofolate reductase gene which confers resistance to methotrexate; the bacterial gpt gene which allows cells to grow in medium containing mycophenylic acid, xanthine and aminopterin; the bacterial hisD gene which allows cells to grow in medium without histidine but containing histidinol; the multidrug resistance gene (mdr) which confers resistance to a variety of drugs; and the bacterial genes which confer resistance to puromycin or phleomycin. All of these markers are dominant selectable and allow chemical selection of most cells expressing these genes.

The expression products encoded by the NOIs may be proteins which are secreted from the cell. Alternatively the NOI expression products are not secreted and are active within the cell. For some applications, it is preferred for the NOI expression product to demonstrate a bystander effect or a distant bystander effect; that is the production of the expression product in one cell leading to the modulation of additional, related cells, either neighbouring or distant (e.g. metastatic), which possess a common phenotype.

The NOIs may be operatively linked to one or more promoter/enhancer elements. Transcription of one or more NOI may be under the control of viral LTRs or alternatively promoter-enhancer elements can be engineered in with the transgene. Preferably the promoter is a strong promoter such as CMV. The promoter may be a regulated promoter. The promoter may be tissue-specific. Suitable promoters include the hypoxia response element (HRE) which promotes gene expression under low oxygen conditions.

NOIs

In the present invention, preferably the EOI is one or more NOIs (nucleotide sequences of interest)—wherein said NOIs may be delivered to a target cell in vivo or in vitro.

If the vector system of the present invention is a viral vector system, then it is possible to manipulate the viral genome so that viral genes are replaced or supplemented with one or more NOIs which may be heterologous NOIs.

The term "heterologous" refers to a nucleic acid or protein sequence linked to a nucleic acid or protein sequence to which it is not naturally linked.

In the present invention, the term NOI includes any suitable nucleotide sequence, which need not necessarily be a complete naturally occurring DNA or RNA sequence. Thus, the NOI can be, for example, a synthetic RNA/DNA sequence, a recombinant RNA/DNA sequence (i.e. prepared by use of recombinant DNA techniques), a cDNA sequence or a partial genomic DNA sequence, including combinations thereof. The sequence need not be a coding region. If it is a coding region, it need not be an entire coding region. In addition, the RNA/DNA sequence can be in a sense orientation or in an anti-sense orientation. Preferably, it is in a sense orientation. Preferably, the sequence is, comprises, or is transcribed from cDNA.

The NOI may encode a protein of interest ("POI"). In this way, the vector delivery system could be used to examine the effect of expression of a foreign gene on the target cell (such as an epithelial cell). For example, the retroviral delivery system could be used to screen a cDNA library for a particular effect on the a cell of the respiratory system or of the brain, motor neuron or CSF.

For example, one could identify new survival/neuroprotective factors for epithelial cells, which would enable transfected cells to persist in the presence of an apoptosis-inducing factor.

In accordance with the present invention, the NOI can be a therapeutic gene—in the sense that the gene itself may be capable of eliciting a therapeutic effect or it may code for a product that is capable of eliciting a therapeutic effect.

In accordance with the present invention, suitable NOIs include those that are of therapeutic and/or diagnostic application such as, but not limited to: sequences encoding cytokines, chemokines, hormones, antibodies, anti-oxidant molecules, engineered immunoglobulin-like molecules, a single chain antibody, fusion proteins, enzymes, immune co-stimulatory molecules, immunomodulatory molecules, anti-sense RNA, a transdominant negative mutant of a target protein, a toxin, a conditional toxin, an antigen, a tumour suppresser protein and growth factors, membrane proteins, vasoactive proteins and peptides, anti-viral proteins and ribozymes, and derivatives thereof (such as with an associated reporter group).

Suitable NOIs for the treatment of retinopathies (such as age-related macular degeneration and proliferative diabetic retinopathy) include angiostatic proteins.

The NOIs may also encode pro-drug activating enzymes, cytotoxic agents and enzyme inhibitors.

Examples of prodrugs include but are not limited to etoposide phosphate (used with alkaline phosphatase; 5-fluorocytosine (with cytosine deaminase); Doxorubin-N-p-hydroxyphenoxyacetamide (with Penicillin-V-Amidase); Para-N-bis (2-chloroethyl)aminobenzoyl glutamate (with Carboxypeptidase G2); Cephalosporin nitrogen mustard carbamates (with B-lactamase); SR4233 (with p450 reductase); Ganciclovir (with HSV thymidine kinase); mustard prodrugs with nitroreductase and cyclophosphamide or ifosfamide (with cytochrome p450).

The expression products encoded by the NOIs may be proteins which are secreted from the cell. Alternatively the NOI expression products are not secreted and are active within the cell. In either event, it is preferred for the NOI expression product to demonstrate a bystander effect or a distant bystander effect; that is the production of the expression product in one cell leading to the killing of additional, related cells, either neighbouring or distant (e.g. metastatic), which possess a common phenotype.

The NOI or its expression product may act to modulate the biological activity of a compound or a pathway. As used herein the term "modulate" includes for example enhancing or inhibiting biological activity. Such modulation may be direct (e.g. including cleavage of, or competitive binding of another substance to a protein) or indirect (e.g. by blocking the initial production of a protein).

The NOI may be capable of blocking or inhibiting the expression of a gene in the target cell. For example, the NOI may be an antisense sequence. The inhibition of gene expression using antisense technology is well known.

The NOI or a sequence derived therefrom may be capable of "knocking out" the expression of a particular gene in the target cell. There are several "knock out" strategies known in the art. For example, the NOI may be capable of integrating in the genome of a epithelial cell so as to disrupt expression of the particular gene. The NOI may disrupt expression by, for example, introducing a premature stop codon, by rendering the downstream coding sequence out of frame, or by affecting the capacity of the encoded protein to fold (thereby affecting its function).

Alternatively, the NOI may be capable of enhancing or inducing ectopic expression of a gene in the target cell. The NOI or a sequence derived therefrom may be capable of "knocking in" the expression of a particular gene.

In one preferred embodiment, the NOI encodes a ribozyme. Ribozymes are RNA molecules that can function to catalyse specific chemical reactions within cells without the obligatory participation of proteins. For example, group I ribozymes take the form of introns which can mediate their own excision from self-splicing precursor RNA. Other ribozymes are derived from self-cleaving RNA structures which are essential for the replication of viral RNA molecules. Like protein enzymes, ribozymes can fold into secondary and tertiary structures that provide specific binding sites for substrates as well as cofactors, such as metal ions. Examples of such structures include hammerhead, hairpin or stem-loop, pseudoknot and hepatitis delta antigenomic ribozymes have been described.

Each individual ribozyme has a motif which recognises and binds to a recognition site in a target RNA. This motif takes the form of one or more "binding arms" but generally two binding arms. The binding arms in hammerhead ribozymes are the flanking sequences Helix I and Helix III which flank Helix II. These can be of variable length, usually between 6 to 10 nucleotides each, but can be shorter or longer. The length of the flanking sequences can affect the rate of cleavage. For example, it has been found that reducing the total number of nucleotides in the flanking sequences from 20 to 12 can increase the turnover rate of the ribozyme cleaving a HIV sequence, by 10-fold (Goodchild, J V K, 1991 Arch Biochem Biophys 284: 386-391). A catalytic motif in the ribozyme Helix II in hammerhead ribozymes cleaves the target RNA at a site which is referred to as the cleavage site. Whether or not a ribozyme will cleave any given RNA is determined by the presence or absence of a recognition site for the ribozyme containing an appropriate cleavage site.

Each type of ribozyme recognizes its own cleavage site. The hammerhead ribozyme cleavage site has the nucleotide base triplet GUX directly upstream where G is guanine, U is uracil and X is any nucleotide base. Hairpin ribozymes have a cleavage site of BCUGNYR, where B is any nucleotide base other than adenine, N is any nucleotide, Y is cytosine or thymine and R is guanine or adenine. Cleavage by hairpin ribozymes takes places between the G and the N in the cleavage site.

More details on ribozymes may be found in "Molecular Biology and Biotechnology" (Ed. R A Meyers 1995 VCH Publishers Inc p831-8320 and in "Retroviruses" (Ed. J M Coffin et al 1997 Cold Spring Harbour Laboratory Press pp 683).

Expression of the ribozyme may be induced in all cells, but will only exert an effect in those in which the target gene transcript is present.

Alternatively, instead of preventing the association of the components directly, the substance may suppress the biologically available amount of a polypeptide of the invention. This may be by inhibiting expression of the component, for example at the level of transcription, transcript stability, translation or post-translational stability. An example of such a substance would be antisense RNA or double-stranded interfering RNA sequences which suppresses the amount of mRNA biosynthesis.

In another preferred embodiment, the NOI comprises an siRNA. Post-transcriptional gene silencing (PTGS) mediated by double-stranded RNA (dsRNA) is a conserved cellular defence mechanism for controlling the expression of foreign genes. It is thought that the random integration of elements such as transposons or viruses causes the expression of dsRNA which activates sequence-specific degradation of homologous single-stranded mRNA or viral genomic RNA. The silencing effect is known as RNA interference (RNAi). The mechanism of RNAi involves the processing of long dsRNAs into duplexes of 21-25 nucleotide (nt) RNAs. These products are called small interfering or silencing RNAs (siRNAs) which are the sequence-specific mediators of mRNA degradation. In differentiated mammalian cells dsRNA >30 bp has been found to activate the interferon response leading to shut-down of protein synthesis and non-specific mRNA degradation. However this response can be bypassed by using 21 nt siRNA duplexes allowing gene function to be analysed in cultured mammalian cells.

In one embodiment an RNA polymerase III promoter, e.g., U6, whose activity is regulated by the presence of tetracycline may be used to regulate expression of the siRNA.

In another embodiment the NOI comprises a micro-RNA. Micro-RNAs are a very large group of small RNAs produced naturally in organisms, at least some of which regulate the expression of target genes. Founding members of the micro-RNA family are let-7 and lin-4. The let-7 gene encodes a small, highly conserved RNA species that regulates the expression of endogenous protein-coding genes during worm development. The active RNA species is transcribed initially as an ~70 nt precursor, which is post-transcriptionally processed into a mature ~21 nt form. Both let-7 and lin-4 are transcribed as hairpin RNA precursors which are processed to their mature forms by Dicer enzyme.

In a further embodiment the NOI comprises double-stranded interfering RNA in the form of a hairpin. The short hairpin may be expressed from a single promoter, e.g., U6. In an alternative embodiment an effective RNAi may be mediated by incorporating two promoters, e.g., U6 promoters, one expressing a region of sense and the other the reverse complement of the same sequence of the target. In a further embodiment effective or double-stranded interfering RNA may be mediated by using two opposing promoters to transcribe the sense and antisense regions of the target from the forward and complementary strands of the expression cassette.

In another embodiment the NOI may encode a short RNA which may act to redirect splicing ('exon-skipping') or polyadenylation or to inhibit translation.

The NOI may also be an antibody. As used herein, "antibody" includes a whole immunoglobulin molecule or a part thereof or a bioisostere or a mimetic thereof or a derivative thereof or a combination thereof. Examples of a part thereof include: Fab, F(ab)'$_2$, and Fv. Examples of a bioisostere include single chain Fv (ScFv) fragments, chimeric antibodies, bifunctional antibodies.

Transduced target cells which express a particular gene, or which lack the expression of a particular gene have applications in drug discovery and target validation. The expression system could be used to determine which genes have a desirable effect on target cells, such as those genes or proteins which are able to prevent or reverse the triggering of apoptosis in the cells. Equally, if the inhibition or blocking of expression of a particular gene is found to have an undesirable effect on the target cells, this may open up possible therapeutic strategies which ensure that expression of the gene is not lost.

The present invention may therefore be used in conjunction with disease models, such as disease models for respiratory tract infections including cystic fibrosis or models for eye diseases such as age-related macular degeneration or proliferative diabetic retinopathy which are known to those skilled in the art.

An NOI delivered by the vector delivery system may be capable of immortalising the target cell. A number of immortalisation techniques are known in the art (see for example Katakura Y et al (1998) Methods Cell Biol. 57:69-91).

An NOI delivered by the vector delivery system may be a selection gene, or a marker gene. Many different selectable markers have been used successfully in retroviral vectors. These are reviewed in "Retroviruses" (1997 Cold Spring Harbour Laboratory Press Eds: J M Coffin, S M Hughes, H E Varmus pp 444) and include, but are not limited to, the bacterial neomycin and hygromycin phosphotransferase genes which confer resistance to G418 and hygromycin respectively; a mutant mouse dihydrofolate reductase gene which confers resistance to methotrexate; the bacterial gpt gene which allows cells to grow in medium containing mycophenylic acid, xanthine and aminopterin; the bacterial hisD gene which allows cells to grow in medium without histidine but containing histidinol; the multidrug resistance gene (mdr) which confers resistance to a variety of drugs; and the bacterial genes which confer resistance to puromycin or phleomycin. All of these markers are dominant selectable and allow chemical selection of most cells expressing these genes.

The term "mimetic" relates to any chemical which may be a peptide, polypeptide, antibody or other organic chemical which has the same binding specificity as the antibody.

The term "derivative" as used herein includes chemical modification of an antibody. Illustrative of such modifications would be replacement of hydrogen by an alkyl, acyl, or amino group.

Diseases

The vector system used in the present invention is particularly useful in treating and/or preventing a disease which is associated with the death or impaired function of cells of the respiratory tract, lung, liver, skin, eye or any epithelial cells. Thus, the vector system is useful in treating and/or preventing diseases including respiratory tract diseases and epithelial cell cancers.

Diseases which may be treated include, but are not limited to: cystic fibrosis, epitheliomas and retinopathies.

Retinopathies include age-related macular degeneration and proliferative diabetic retinopathy. Both diseases are caused by inappropriate, unregulated and aberrant blood vessel growth (angiogenesis) as a consequence of angiogenic factor (VEGF) expression induced under hypoxic conditions in the retina.

Pharmaceutical Compositions

The present invention also provides the use of a vector delivery system in the manufacture of a pharmaceutical composition. The pharmaceutical composition may be used to deliver an EOI, such as an NOI, to a target cell in need of same.

The pharmaceutical composition may be used for treating an individual by gene therapy, wherein the composition comprises or is capable of producing a therapeutically effective amount of a vector system according to the present invention.

The method and pharmaceutical composition of the invention may be used to treat a human or animal subject. Preferably the subject is a mammalian subject. More preferably the subject is a human. Typically, a physician will determine the actual dosage which will be most suitable for an individual subject and it will vary with the age, weight and response of the particular patient.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as (or in addition to) the carrier, excipient or diluent, any suitable binder(s), lubricant(s), suspending agent(s), coating agent(s), solubilising agent(s), and other carrier agents that may aid or increase the viral entry into the target site (such as for example a lipid delivery system).

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavemosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

In a preferred embodiment, the pharmaceutical composition of the present invention is administered through inhalation or other non-parenteral method.

Diseases which may be treated include, but are not limited to cancer, heart disease, stroke, cystic fibrosis, chronic pulmonary fibrosis, neurodegenerative disease, arthritis, viral infection, bacterial infection, parasitic infection, diseases of the immune system, viral infection, tumours, blood clotting disorders, and genetic diseases—such as chronic granulomatosis, Lesch-Nyhan syndrome, Parkinson's disease, empysema, phenylketonuria, sickle cell anaemia, α-thalasemia, β-thalasemia, Gaucher disease.

Target cells for gene therapy using retroviral vectors include but are not limited to epithelial cells and other cells such as haematopoietic cells, (including monocytes, macrophages, lymphocytes, granulocytes, or progenitor cells of any of these); endothelial cells, tumour cells, stromal cells, astrocytes, or glial cells, muscle cells, epithelial cells, neurons, fibroblasts, hepatocyte, astrocyte, and lung cells.

Within the retroviral vector of the present invention, the one or more NOIs can be under the transcriptional control of the viral LTRs. Alternatively, a combination of enhancer-promoter elements can be present in order to achieve higher levels of expression. The promoter-enhancer elements are preferably strongly active or capable of being strongly induced in the target cells. An example of a strongly active promoter-enhancer combination is a human cytomegalovirus (HCMV) major intermediate early (MIE) promoter/enhancer combination. The promoter-enhancer combination may be tissue or temporally restricted in their activity. Examples of a suitable tissue restricted promoter-enhancer combinations are those which are highly active in tumour cells such as a promoter-enhancer combination from a MUC1 gene or a CEA gene.

Hypoxia or ischaemia regulatable expression may also be particularly useful under certain circumstances. Hypoxia is a powerful regulator of gene expression in a wide range of different cell types and acts by the induction of the activity of hypoxia-inducible transcription factors such as hypoxia inducible factor-1 (HIF-1) (Wang and Semenza 1993 PNAS. (USA) 90: 430) which bind to cognate DNA recognition sites, the hypoxia responsive elements (HREs) on various gene promoters. A multimeric form of HRE from the mouse phosphoglycerate kinase-1 (PGK-1) gene has been used to control expression of both marker and therapeutic genes by human fibrosarcoma cells in response to hypoxia in vitro and within solid tumours in vivo (Firth et al 1994, PNAS 91(14): 6496-6500; Dachs et al 1997 Nature Med. 5: 515). In retinopathies, where damage has occurred in hypoxic regions due to VEGF expression, the use of HRE which promotes gene expression in low oxygen conditions can be used to target gene expression in retinal cells.

Alternatively, the fact that glucose deprivation is also present in ischaemic areas of tumours can be used to activate heterologous gene expression especially in tumours. A truncated 632 base pair sequence of the grp 78 gene promoter, known to be activated specifically by glucose deprivation, has been shown to be capable of driving high level expression of a reporter gene in murine tumours in vivo (Gazit et al 1995 Cancer Res. 55: 1660.).

Various preferred features and embodiments of the present invention will now be described in more detail by way of non-limiting examples.

EXAMPLES

Example 1

Pseudotyping with Influenza HA Alone

Equine infectious anemia virus (EIAV) retroviruses were pseudotyped with influenza HA. Transfections were carried out in the human kidney cell line 293T (as described in Soneoka et al., 1995) to produce the vector virions. The efficiency of pseudotyping was studied by assessing the viral titres for these pseudotyped vectors. The resulting viral titres for EIAV pseudotyped with influenza HA were relatively low.

Example 2

Pseudotyping with Influenza HA and M2

We investigated whether gene transfer efficiency could be improved by expression of the influenza M2 protein in cells producing vectors derived from equine infectious anemia virus (EIAV).

The effect of fowl plague virus (FPV) M2 expression on HA pseudotyped EIAV vector production was tested.

First, vectors were prepared by transient transfection of 293T cells.

293T cells (obtained from Tal Kafri, University of North Carolina) were maintained in Dulbecco's modified Eagle's medium (DMEM-H, Gibco/Invitrogen Life Technologies, Carlsbad, Calif.) containing 10% (v/v) fetal calf serum. Transient transfections were performed on 293T cells by using a modified calcium phosphate technique (Graham, F. L., and van der Eb, A. J. (1973) *Virology* 52: 456-67) as described previously (Comstock et al. (1997) *Methods Mol Biol* 62: 207-22).

The transfection reactions contained four plasmids including: the EIAV lacZ vector SIN-6.1 CZW, the EIAV gag-pol-rev expression vector pEV53B (Olsen, J. C. (1998) *Gene Ther* 5: 1481-7), the FPV HA expression pCMV-HA (Hatziioannou et al. (1998) *J Virol* 72: 5313-7), and various amounts of the FPV M2 expression vector pCB6-M2 (Henkel, J. R., and Weisz, O. A. (1998) *J Biol Chem* 273: 6518-24).

After overnight transfection, the medium was changed to DMEM-H containing 7 milliunits bacterial neuraminidase (*Vibrio cholerae*, Calbiochem-Novabiochem Corporation, LaJolla, Calif.) per ml. The HA pseudotyped SIN6.1 CZW vector-containing supernatant was harvested from the cells 24 hours later and filtered through 0.45 µm filters.

To determine relative transduction efficiency, 293T cells were plated onto 12-well culture dishes at a density of $4.4 \times 10^4$ cells/cm² the day before infection. One ml of medium (containing appropriate dilutions of the original virus stock) was added to each well with 8 µg/ml polybrene (Sigma Chemical Co., St. Louis Mo.) and incubated for two hours. The virus was removed and replaced with growth medium. At 48 hours after infection, the medium was removed, cells washed once with 1 ml PBS and cell lysates (200 µl) were prepared for assay of β-galactosidase activity using a chemiluminescence assay kit (Galacto-Light Plus, Tropix, Bedford, Mass.). The lysates were prepared and assayed according to the manufacture's recommendations. The concentration of cellular protein was determined by using a BCA Protein Assay Reagent Kit (Pierce, Rockford, Ill.).

Figure 2:
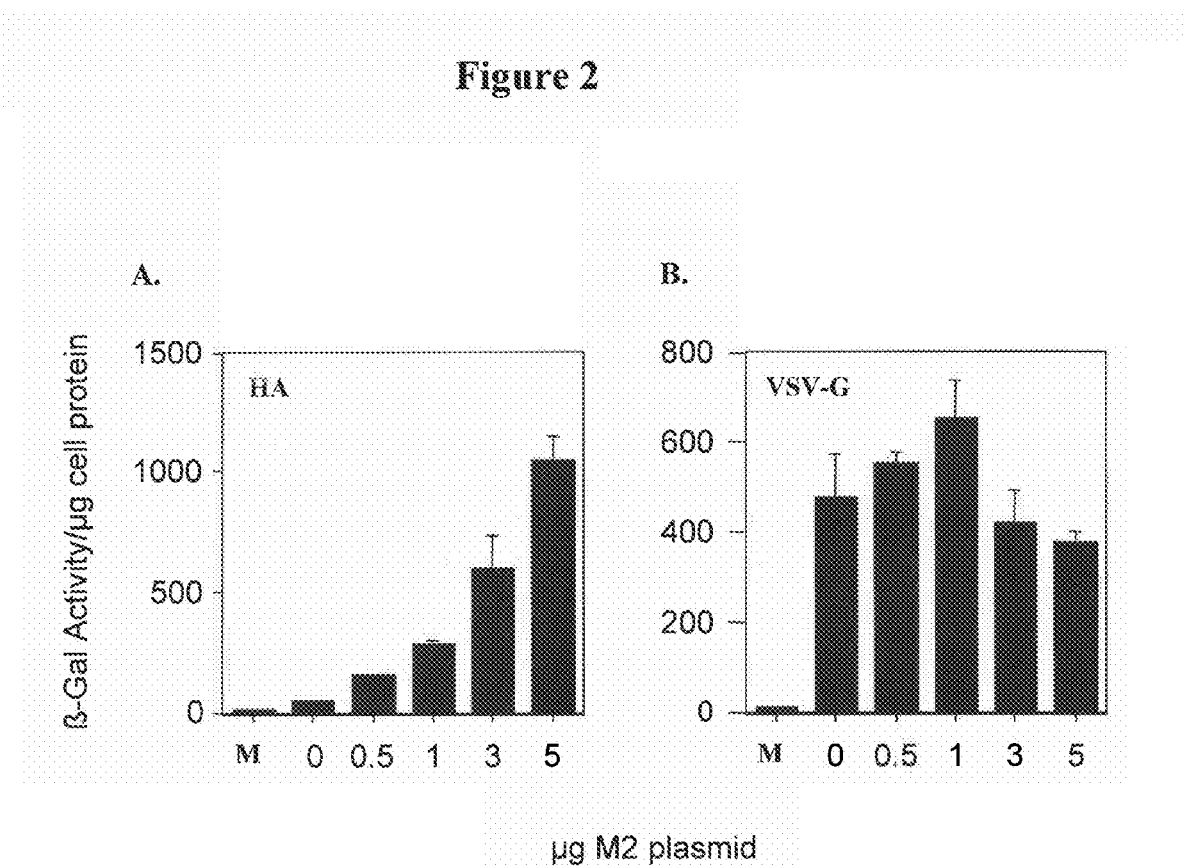
FIGS. 2A and 2B show that influenza M2 augments influenza HA pseudotyping of EIAV vectors but does not enhance VSV-G pseudotyping. The SIN-6.1CZW vector was pseudotyped with VSV-G or FPV HA in transfection reactions containing the indicated amounts of the FPV M2 expression plasmid pCB6 M2. Producer cells were treated with bacterial neuraminidase. The viral vectors were used to transduce 293T cells and 48 hours post-transduction the β-Gal activity in cell lysates was measured. M indicates mock transfected controls.

FIG. 2 shows the effect of expression of FPV M2 cDNA in EIAV vector producing cells. Expression of M2 greatly improved HA-vector production in a dose-dependent manner. At the highest dose (5 µg) of M2 expression plasmid used, a 30-fold increase in vector production was observed. In control experiments, M2 had no pseudotyping activity alone.

In parallel transfection reactions the effect of M2 expression on VSV-G pseudotyped vector production was determined (FIG. 2). It was found that M2 expression did not enhance VSV-G pseudotyping. Thus the effect of FPV M2 to augment FPV HA pseudotyping is not due to non-specific effects on transfection efficiency.

Example 3

Synergism of M2 Expression and NA Treatment

Figure 3:
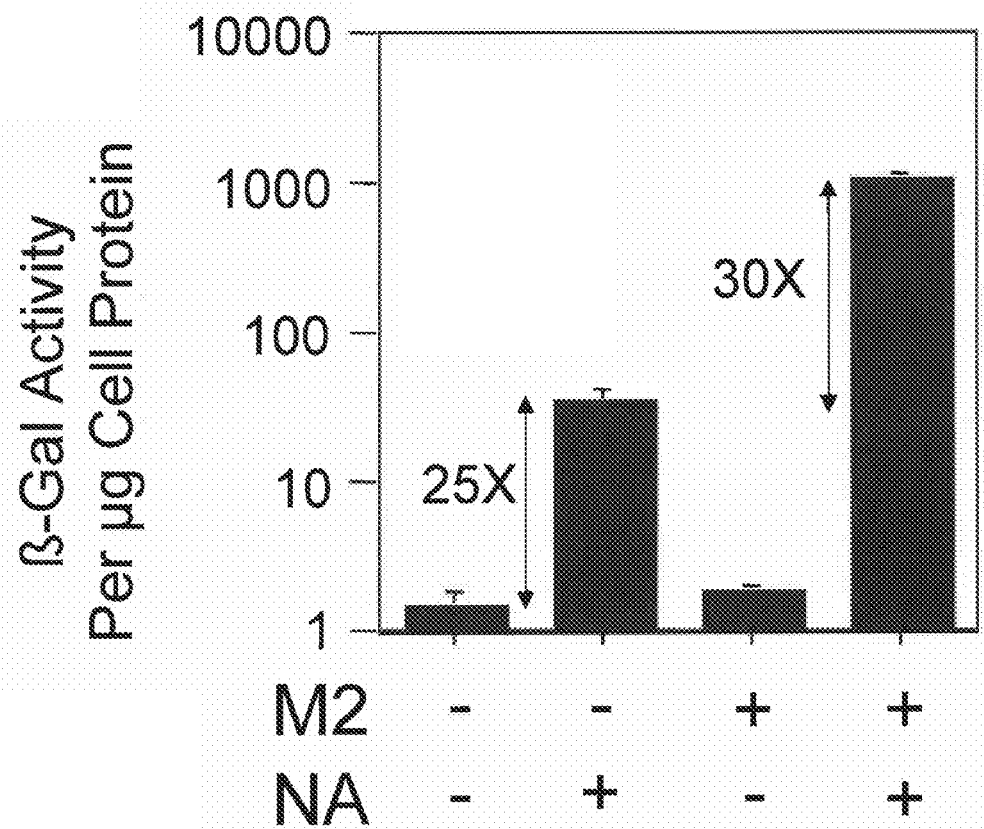
FIG. 3 shows synergism of M2 and NA for influenza HA pseudotyping of EIAV lacZ vector. The SIN-6.1CZW vector was pseudotyped with FPV HA in transfection reactions containing or lacking the FPV M2 expression plasmid pCB6 M2. Producer cells were either treated or untreated with bacterial neuraminidase. Vector preparations were used to transduce 293T cells and 48 hours post-transduction the β-gal activity in cell lysates was measured.
Figure 4:
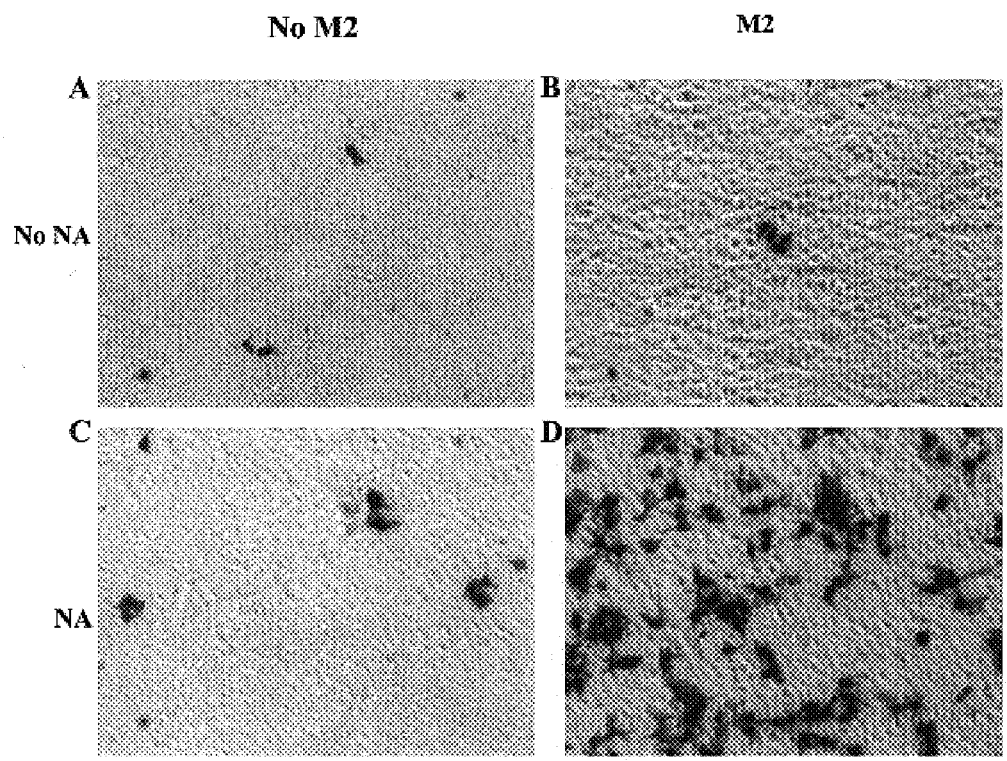
FIGS. 4A-4D show gene transfer to human 293T cells by HA pseudotyped EIAV lacZ vector produced in the presence or absence of M2 expression and NA treatment. The SIN-6.1CZW vector was pseudotyped with FPV HA in transfection reactions containing or lacking the FPV M2 expression plasmid pCB6 M2. Producer cells were either treated or untreated with bacterial neuraminidase. Vector preparations were used to transduce 293T cells and 48 hours post-transduction the cells were fixed with glutaraldehyde and stained with X-Gal.

The requirements for NA treatment of producer cells in the presence or absence of M2 expression were determined (FIG. 3). In the absence of NA, only a low level of vector was produced as determined by measuring β-gal activity in lysates of transduced cells (FIG. 3) or by staining transduced cells with X-Gal (FIG. 4). The titres of SIN-6.1CZW(HA) produced in the absence of NA, as determined by X-Gal staining were about $10^2$ TU/ml. NA treatment alone increased vector production approximately 25-fold. Both NA treatment and M2 expression resulted in a 750-fold increase in vector production (FIG. 3).

Example 4

Amantadine Inhibits M2 Augmentation of Vector Production

To confirm the role of M2 in HA pseudotyping, we produced vectors in the presence of amantadine, which acts specifically to inhibit the ion channel activity of influenza M2. (Wang et al. (1993) *J Virol* 67: 5585-94). At micromolar concentrations, amantadine has been shown to be an effective inhibitor of influenza virus replication in cell culture (Neumayer et al. (1965) *Proc Soc Exp Med Biol* 119: 393-396).

The effect of amantadine on SIN-6.1CZW(HA) EIAV vector production was tested. Various concentrations were added to vector producing cells and these concentrations were maintained on transduced cells until vector was harvested for determination of transduction efficiency.

Figure 5:
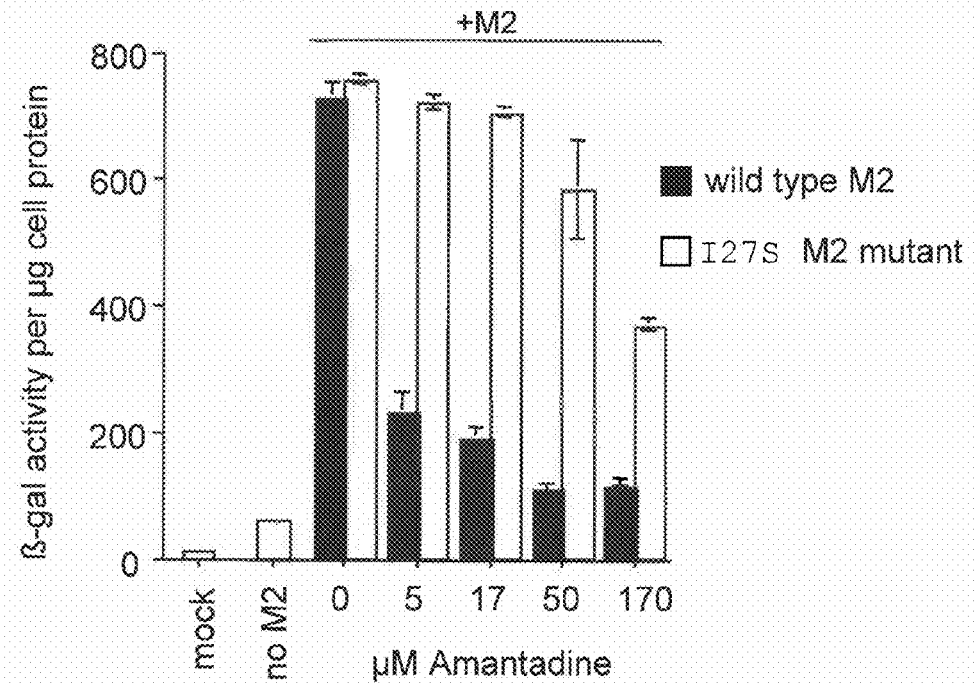
FIGS. 5A and 5B show amantadine inhibits the augmentation of HA pseudotyping by M2. The SIN-6.1 CZW vector was pseudotyped in transfection reactions with FPV HA and either wild type FPV M2 or the amantadine-resistant I27S mutant of M2 (5A) or VSV-G (5B). The 293T cells were treated for 12 hours prior to transfection with the indicated amounts of amantadine. Amantadine was maintained in cultures at the indicated concentrations during vector production. Viral vector preparations were harvested and used to transduce 293T cells. At 48 hours post-transduction the 13-gal activity in cell lysates was measured.
Figure 5:
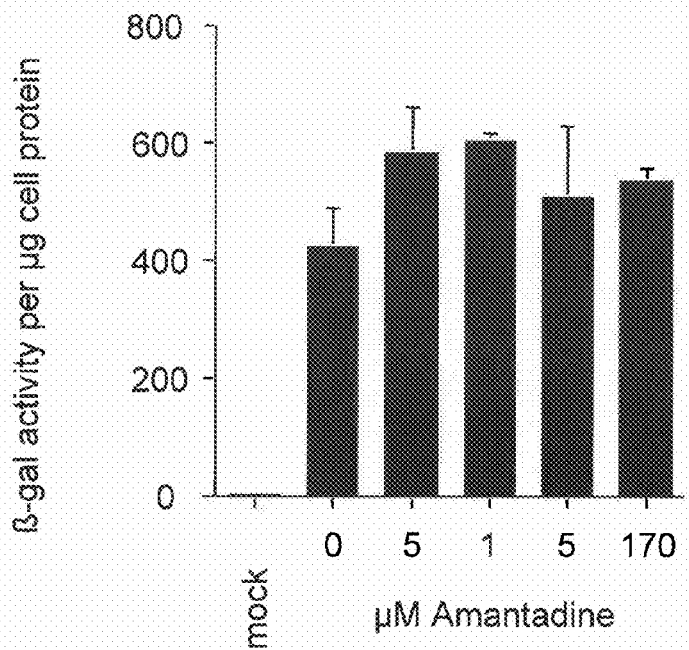

It was found that amantadine had a potent dose-dependent effect on vector production (FIG. 5A). Amantadine inhibited M2 augmented vector product by 70% at a concentration of 5 µM.

The specificity of amantadine inhibition was tested in two ways.

First, the effect of amantadine on VSV-G pseudotyping was determined. It was found that for concentrations of 5 µM to 50 µM, amantadine did not affect pseudotyping of SIN-6.1CZW by VSV-G (FIG. 5B). VSV replication has previously been shown to be refractory to amantadine inhibition.

In a second approach, the effect of amantadine on an M2 mutant carrying a single amino acid change, I27S, was tested. The I27S mutation is thought to affect the interaction of amantadine with the M2 protein (Sansom et al. (1998) *Bioessays* 20: 992-1000) and results in amantadine-resistant M2 ion channel activity (Hay et al. (1985) *EMBO J.* 4: 3021-4). It was found that in comparison to wild-type M2, EIAV vector production in cells expressing the I27S M2 was significantly more resistant to inhibition by amantadine (FIG. 5A). These results suggest that the ion channel activity of M2 is critical for M2 augmentation of HA pseudotyping.

Example 5

Role of M2 During HA-Mediated EIAV Vector Gene Transfer

To determine if M2 has a role early after infection by EIAV vectors, the SIN-6.1CZW(HA) vector was produced by transient transfection in the presence of M2 and the absence of amantadine. The vector was then used to transduce 293T cells that had been pre-incubated with various concentrations of amantadine. As a control, VSV-G pseudotyped vector was produced and used in parallel infections.

Figure 6:
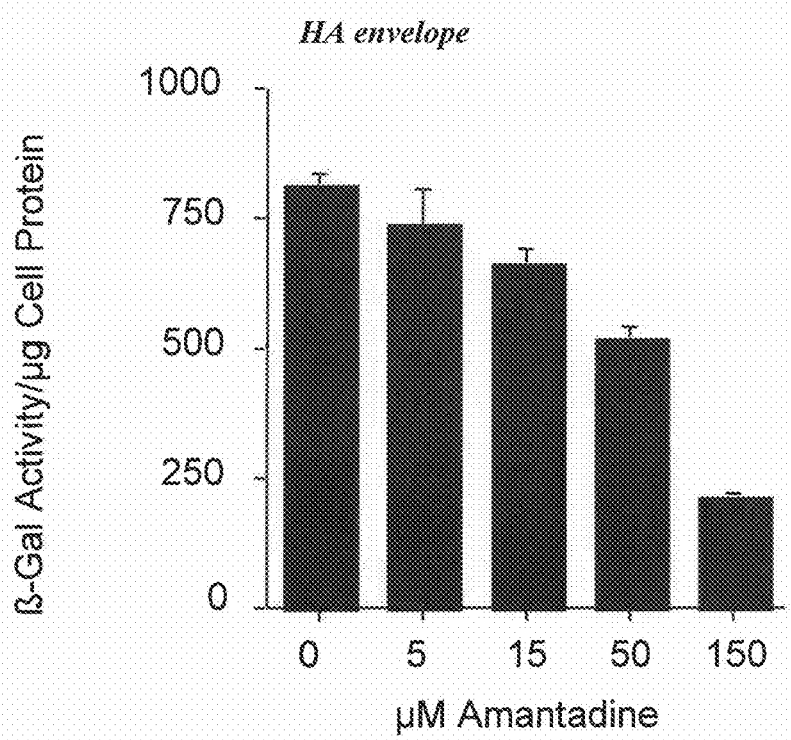
FIGS. 6A and 6B show the role of M2 during HA-mediated EIAV vector gene transfer. The SIN-6.1 CZW vector was pseudotyped in transfection reactions with FPV HA/M2 or VSV-G in the absence of amantadine. Vector preparations were use to transduce 293T cells in the presence of the indicated concentrations of amantadine. The 293T cells had been treated with the indicated concentrations of amantadine for 12 hours prior to transduction. At 48 hours post-transduction the β-gal activity in cell lysates was measured.
Figure 6:
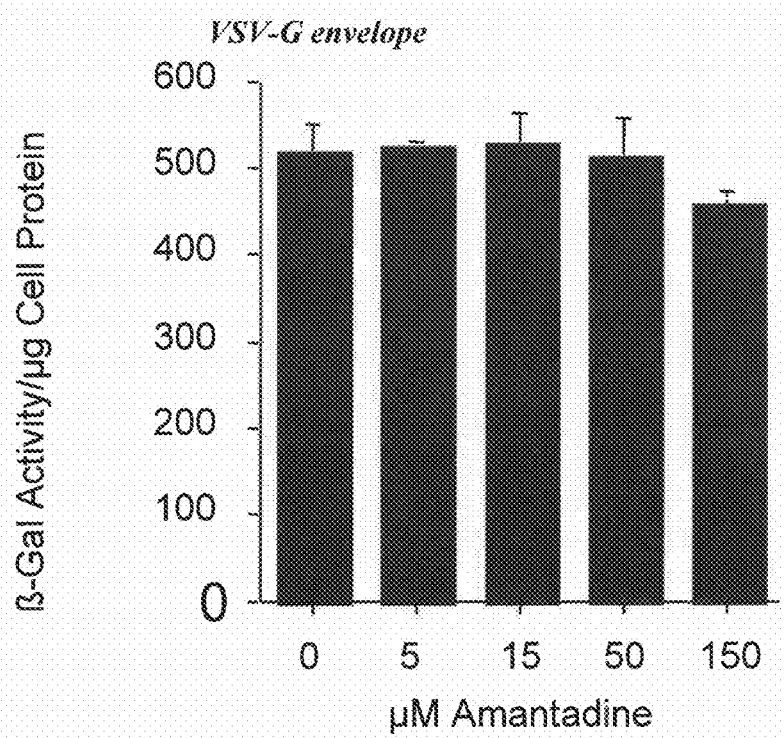

The results of this experiment are shown in FIG. 6. It was found that amantadine affected the gene transfer step of the HA pseudotyped vector, but did not affect gene transfer by the VSV-G pseudotyped vector. Higher doses were required to inhibit transduction than to inhibit vector production (compare FIGS. 5 and 6). Nevertheless, the amantadine sensitivity suggests that the ion channel activity of M2 plays a role during transduction of target cells.

Example 6

Concentration of Influenza HA Pseudotyped Retroviral Vectors

An important consideration for the use of pseudotyped EIAV vectors in gene transfer experiments for in vivo applications is the ability to concentrate vectors. Thus, we have investigated whether we can increase the viral titre by concentrating the viral supernatant using ultracentrifugation (Burns et al., 1993 PNAS 90:8033-8037).

It was determined that the infectivity of M2-enhanced HA pseudotyped EIAV vectors could be recovered after pelleting in an ultracentrifuge.

In this experiment, 500 ml of SIN-6.1 CZW(HA)-containing supernatant from a four plasmid (SIN-6.1CZW(HA)/EV53B/FPV HA/CB6 M2) co-transfection of 293T cells was concentrated by centrifugation in a high-speed centrifuge (6000×g, 24 hours). The pellet was suspended in 0.5 ml of 1× Hank's Balanced Salt Solution (HBSS) to achieve a 1000-fold concentration of virus particles. Either 1 µl or 3 µl of concentrated vector was diluted to 1 ml, to give final concentrations of 1× or 3×, respectively, and used to infect 293T cells.

Figure 7:
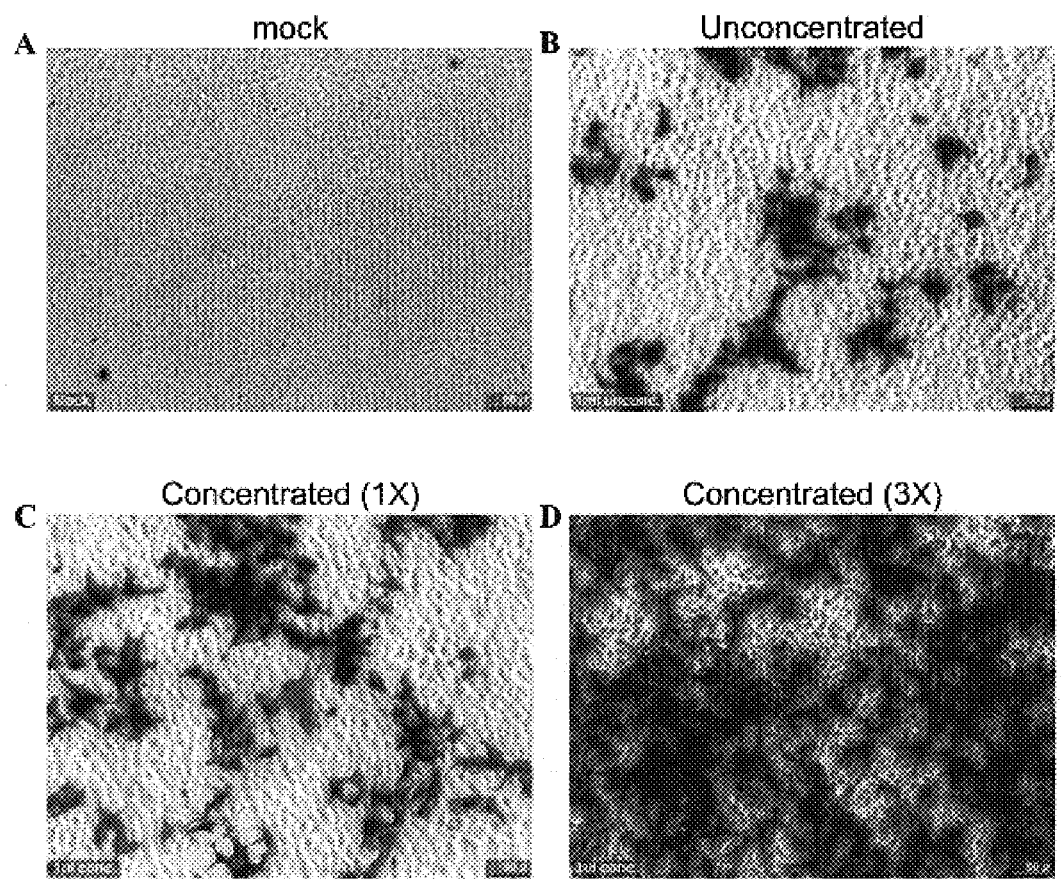
FIGS. 7A-7D show concentration of the HA pseudotyped SIN-6.1CZW vector by pelleting using centrifugation. The SIN-6.1CZW EIAV vector was pseudotyped with influenza HA and concentrated by pelleting in a high-speed centrifuge (6000×g, 24 hours). The vector pellet was dissolved in a volume 1000-fold less than the volume before centrifugation. Either 1 μl or 3 μl of the concentrated vector stock was diluted to 1 ml to give final concentrations of 1× or 3×, respectively, and used to infect human 293T cells. Cells were stained with X-Gal 72 hr post-transduction.

FIG. 7 shows 293T cells treated with unconcentrated or concentrated HA-pseudotyped SIN-6.1CZW and stained with 1 mg/ml X-Gal 72 hr post-transduction. Cells were visualized using an Olympus inverted microscope at 20× power.

No loss of infectivity was observed following reconstitution of the concentrated stock to the original 1× dilution (1 µl concentrate diluted to 1 ml). Furthermore, the 3× concentrated virus (3 µl concentrate diluted to 1 ml) resulted in higher transduction efficiency suggesting that infectivity can be increased by concentrating the virus by pelleting using centrifugation techniques.

In the presence of M2, it was possible to produce vectors with titres greater than 10e5 transducing particles per ml with influenza HA/M2 pseudotyped EIAV. With ultracentrifugation, the titre was increased to greater than 10e8 transducing particles per ml.

The ability to concentrate vectors make pseudotyping with the influenza HA and a second membrane protein an attractive proposal for easy targeting of retroviral vectors carrying any therapeutic gene to a broad range of cells.

Example 7

Expression of Influenza NA cDNA in EIAV Vector Producing Cells

In the experiments described above and in previously published studies, bacterial NA was added to producer cells to enable release of virus particles by preventing the interaction of HA with cell-associated sialic acid.

Figure 8:
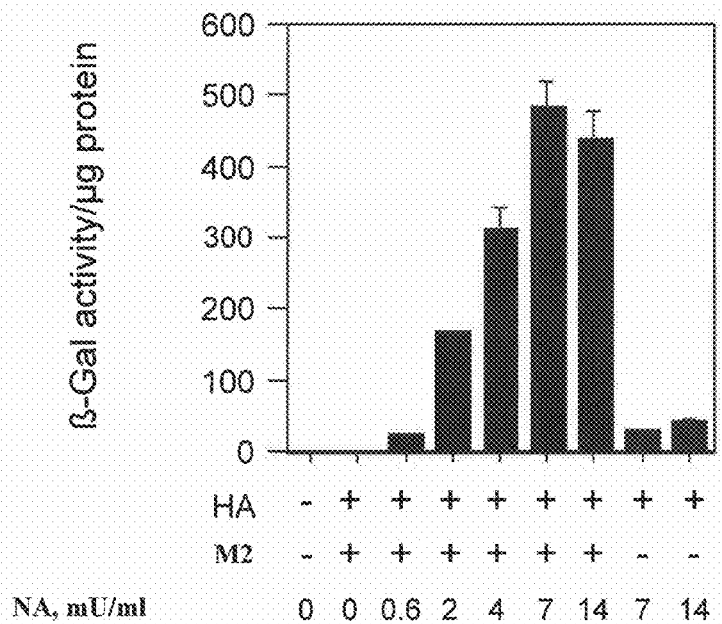
FIGS. 8A and 8B show a comparison of the use of influenza NA cDNA vs. bacterial NA enzyme to treat producer cells. The SIN-6.1CZW EIAV vector was pseudotyped with influenza HA/M2 using increasing amounts of bacterial neuraminidase (NA) (*Vibrio cholerae*, Calbiochem-Novabiochem Corporation, LaJolla, Calif.) (8A) or increasing amounts of influenza NA cDNA (8B) to release bound HA-pseudotyped vector from producer cells. Viral vector preparations were harvested and used to transduce 293T cells. At 48 hours post-transduction the β-gal activity in cell lysates was measured.
Figure 8:
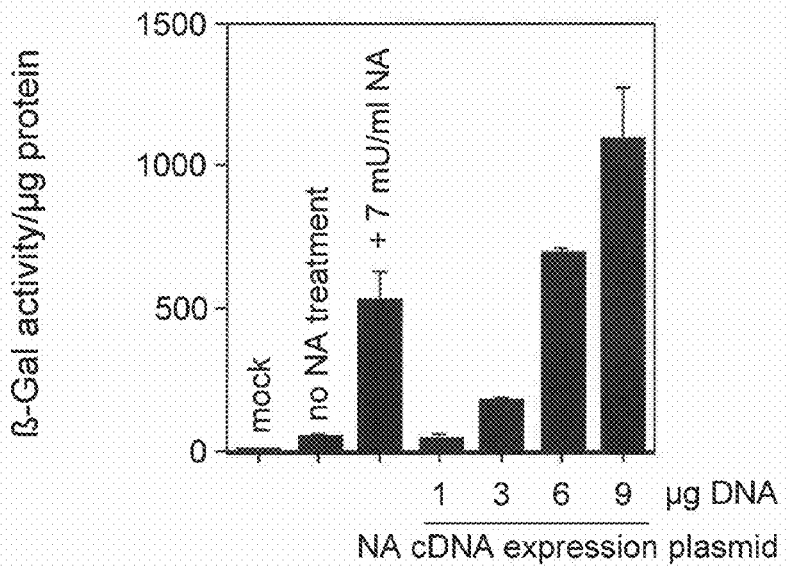

FIG. 8A shows a dose-titration of added purified bacterial NA enzyme on vector production. The SIN-6.1CZW EIAV vector was pseudotyped with influenza HA/M2 using increasing amounts of bacterial neuraminidase (NA) (*Vibrio cholerae*, Calbiochem-Novabiochem Corporation, LaJolla, Calif.). Optimal vector production was observed when vector-producing cells were treated with 7 milliunits NA/ml serum-free cell culture medium.

It was tested whether vectors could be produced in cells expressing influenza NA cDNA. In this case an NA cDNA from influenza A/PR/8/34 (H1N1) was prepared by PCR amplification of the NA gene from purified virus and expressed from a plasmid expression vector (pEF-NA) during vector production.

The results in FIG. 8B show that expression of influenza NA cDNA leads to a dose-dependent increase in vector production. Viral vector preparations were harvested and used to transduce 293T cells. At 48 hours post-transduction the B-gal activity in cell lysates was measured. At the highest levels of NA cDNA used, approximately two-fold higher vector titres were obtained than with the optimal levels of bacterial NA enzyme treatment.

Example 8

Host Range of HA Pseudotyped EIAV Vectors

The HA pseudotyped SIN-6.1CZW vector produced in cells expressing influenza M2 and NA cDNAs was used to measure the ability of HA env to transduce a variety of mammalian and avian cell lines.

The SIN-6.1CZW EIAV vector was pseudotyped with influenza HA/M2/NA or VSV-G and used to transduce various cell lines at 30-50% confluency using serially diluted virus stocks. At 48 hours post-infection, the cells were stained with X-Gal and the titre was determined by counting blue foci.

Figure 9:
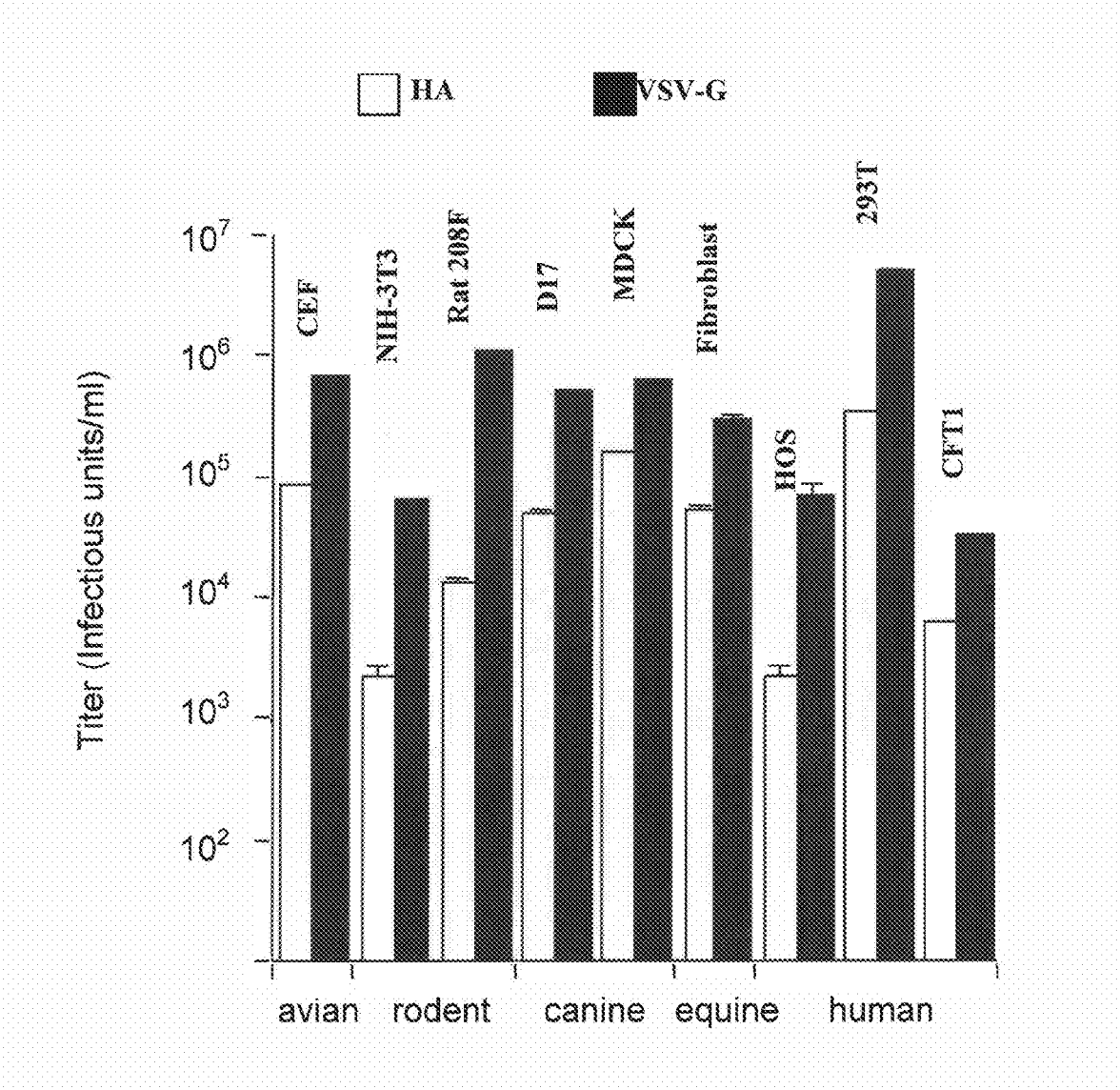

The vector transduced cells were derived from primary chicken fibroblasts and mammalian cell lines derived from humans, rodents, horses and dogs (FIG. 9). No obvious preference for cells from any species was observed.

Compared to VSV-G pseudotyped virus, the efficiency of transduction for a given cell line by HA pseudotyped virus was consistently 10-100 fold lower with the highest HA titres ($>10^5$ infectious units/ml) observed on human 293T cells and canine MDCK cells.

Example 9

M2 Augmentation of HA Pseudotyped MuLV Vectors and HA Pseudotyped HIV Vectors

To determine if the M2 augmentation of pseudotyping was limited to equine lentiviral vectors or applied also to other retroviruses, the requirements for HA pseudotyping of vectors derived from MuLV and HIV-1 were determined.

The SIN-6.1CZW EIAV vector or the pLenti6/V5-GW/lacZ (Invitrogen Corporation, Carlsbad, Calif.) HIV-1 lentiviral vectors or the HIT-SIN-CZ Moloney murine leukemia virus (MuLV) vector (Wilcox et al. (1999) *Proc Natl Acad Sci USA* 96: 9654-9) were pseudotyped with HA in the presence or absence of influenza M2 and/or M2 and used to infect 293T cells. At 48 hours post-transduction the β-gal activity in cell lysates was measured.

Figure 10:
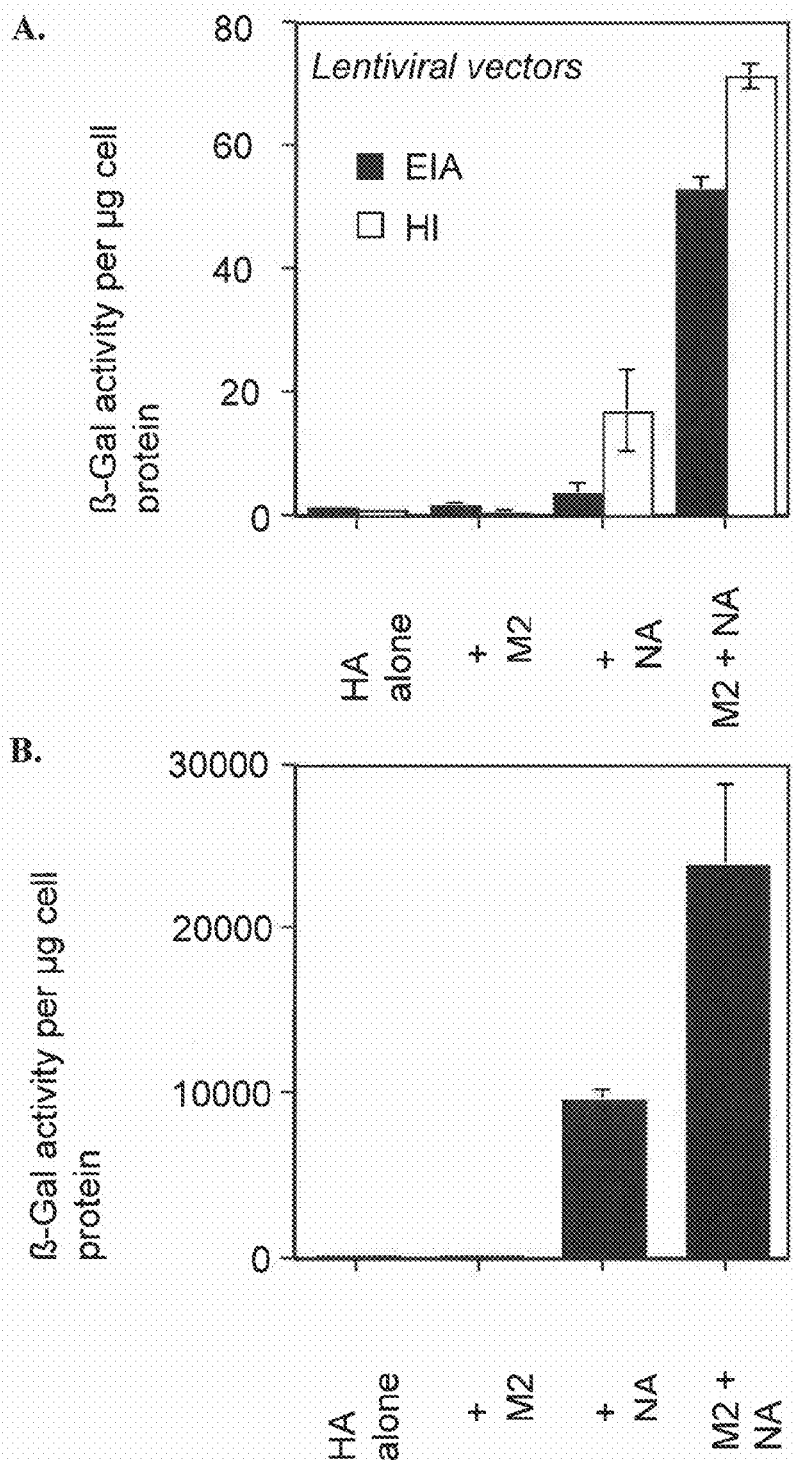
FIGS. 10A and 10B show enhancement of HA pseudotyping of HIV-1 and EIAV lentiviral vectors, and MuLV retroviral vectors by M2 and NA. The SIN-6.1CZW EIAV vector or the pLenti6/V5-GW/lacZ (Invitrogen Corporation, Carlsbad, Calif.) HIV-1 lentiviral vectors (10A) or the HIT-SIN-CZ Moloney murine leukemia virus (MuLV) vector (10B) (Wilcox et al. (1999) *Proc Natl Acad Sci USA* 96: 9654-9) were pseudotyped with HA in the presence or absence of influenza M2 and/or M2 and used to infect 293T cells. At 48 hours post-transduction the β-gal activity in cell lysates was measured.

The results (FIG. 10) indicated that HA-pseudotyped vector production was enhanced by M2 for MuLV and HIV-1 as with EIAV. In these experiments, the titres obtained for HA pseudotyping of EIAV and HIV lentiviral vectors in the presence of HA and NA were similar (~$10^5$ infectious units/ml) whereas, the titres obtained for pseudotyping the MuLV vector HIT-SIN-CZ were significantly higher (~$4 \times 10^6$ infectious units/ml).

Example 10

HA/M2 Pseudotyped Vectors Enable Efficient Transduction of Polarized MDCK Cells and Human Airway Epithelial Cells The ability of HA pseudotyped vectors to transduce the apical side of polarized epithelia was tested. The apical side of polarized epithelia have proved difficult to transduce by other means.

Figure 11:
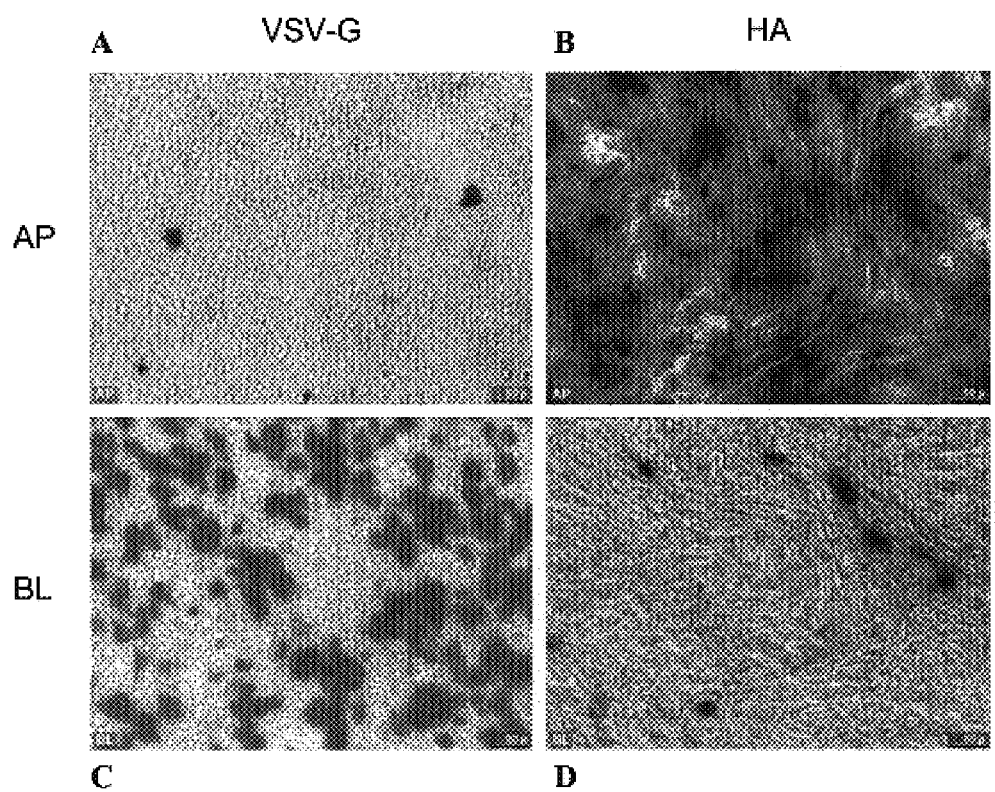
FIGS. 11A-11D show gene transfer of HA-pseudotyped EIAV lacZ vector to polarized Madin-Darby Canine Kidney (MDCK) cells. The apical (AP) or basolateral (BL) surface of polarized MDCK cells (Rt >800 Ω cm$^2$) on 0.4 µm T-Col membranes was exposed to an EIAV lacZ vector (SIN-6.1CZW) pseudotyped with VSV-G or influenza HA/M2/NA at a multiplicity of infection (MOI) of 10. The cultures were stained with X-Gal 72 hours post-transduction.

The apical (AP) or basolateral (BL) surface of polarized Madin-Darby Canine Kidney (MDCK) cells (Resistance>800 Ω $cm^2$) on 0.4 μm collagen coated permeable membranes (Transwell-Col, Corning Inc., Corning, N.Y.) was exposed to an EIAV lacZ vector (SIN-6.1CZW) pseudotyped with VSV-G or the influenza HA, M2, and NA membrane proteins at a multiplicity of infection (MOI) of 10. The cultures were stained with X-Gal 96 hours post-transduction. The HA-pseudotyped vector was found to preferentially transduce polarized MDCK cells from the apical surface (FIG. 11). In contrast, EIAV pseudotyped with vesicular stomatitis virus protein G (VSV-G) only transduced from the basolateral surface.

The time course of lacZ gene expression was determined by quantifying 13-gal activity in MDCK cell lysates using a chemiluminescence assay. The SIN-6.1CZW EIAV vector was pseudotyped with either influenza HA/M2/NA or VSV-G envelope and used to transduce the apical or basolateral surface of polarized MDCK cells grown on permeable collagen-coated membrane supports. The resistance of the cultures was >800 ohm·$cm^2$ at the time of infection. Lysates for determining β-galactosidase activity were prepared at the indicated times following infection.

Figure 12:
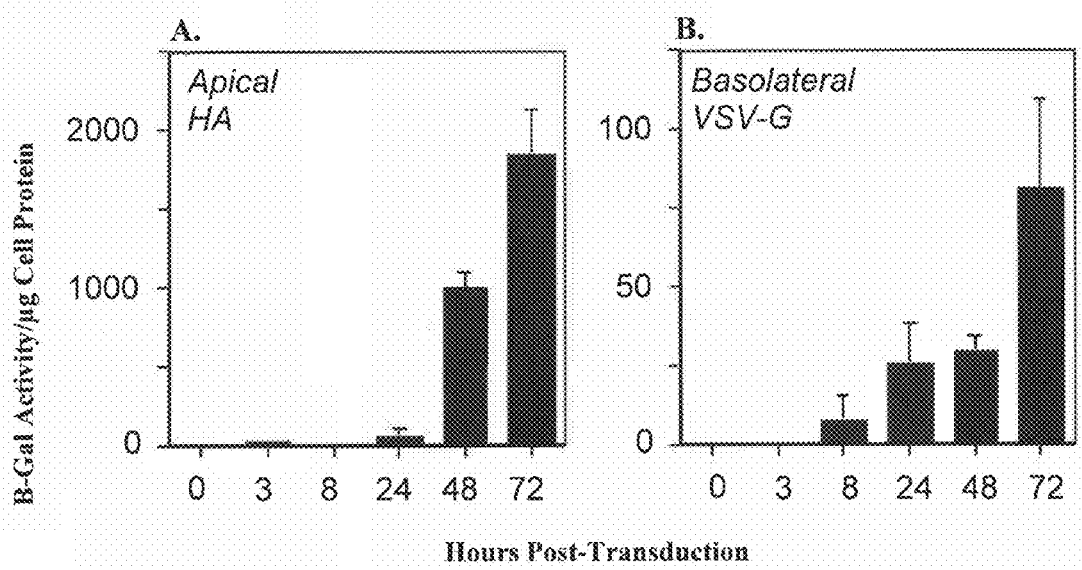
FIGS. 12A and 12B show gene transfer to polarized MDCK cells: Time course of gene expression by HA and VSV-G pseudotyped EIAV lacZ vectors. The SIN-6.1CZW EIAV vector was pseudotyped with either influenza HA/M2/NA or VSV-G envelope and used to transduce the apical or basolateral surface of polarized MDCK cells grown on permeable collagen-coated membrane supports. The resistance of the cultures was >800 ohm·cm$^2$ at the time of infection. Lysates for determining β-galactosidase activity were prepared at the indicated times following infection.

FIG. 12 shows that the time course of gene expression was similar for both HA and VSV-G pseudotyped vectors exposed to the apical and basolateral surfaces, respectively.

Example 11

HA Pseudotyped EIAV Lentiviral Vector Gene Transfer to Mouse Trachea in Vivo

Direct in vivo delivery to the trachea of mice was tested using the double tracheostomy technique for delivery to the tracheas of anesthetized mice (Johnson et al. (1998) *J Virol* 72: 8861-72; Johnson et al. (2000) *Gene Ther* 7: 568-74).

For these experiments the HA pseudotyped EIAV SIN-6.1CZW vector was prepared by co-transfection of 293T cells with pSIN-6.1CZW, pEV53B, pCMV-HA, and pCB6-M2. Purified bacterial NA was used to treat vector-producing cells. The vector was concentrated by high-speed centrifugation to a titre of $2 \times 10^8$ infectious units/ml.

Double tracheotomies were performed on 3-week-old anesthetized mice (n=3). $4 \times 10^6$ infectious units (20 μl) of the concentrated EIAV SIN-6.1CZW (HA/M2) vector was instilled into the proximal tracheostomy (Estimated multiplicity of infection (MOI)=10). The vector dwell time was 2 hr.

Figure 13:
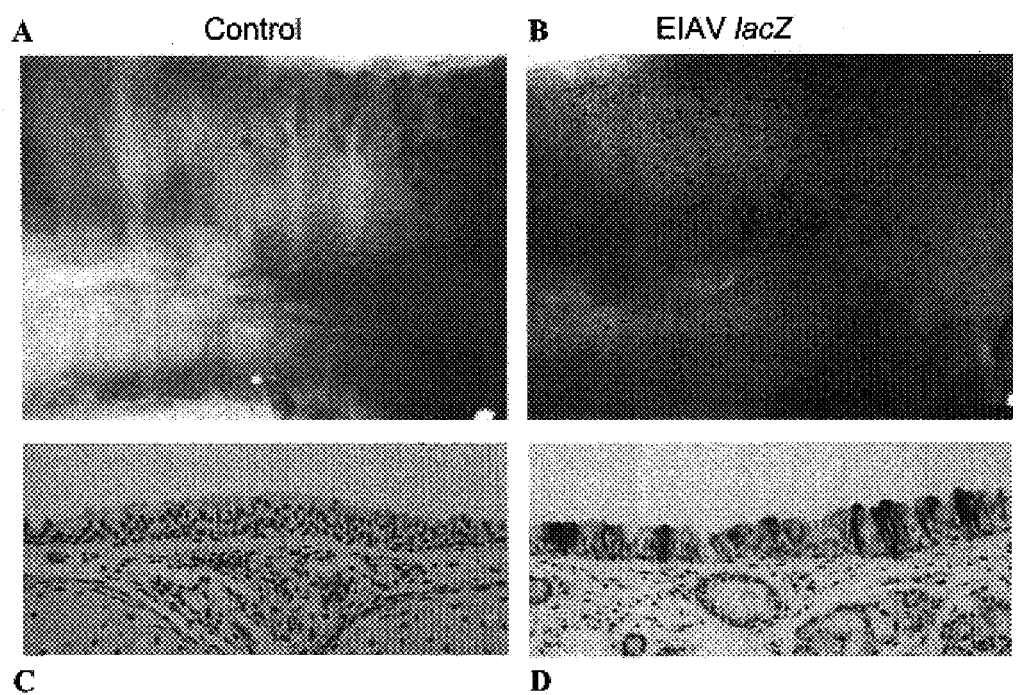
FIGS. 13A-13D show gene transfer to uninjured mouse trachea by HA pseudotyped EIAV lacZ vector. Double tracheotomies were performed on 3-week-old anesthetized mice (n=3). 4×10$^6$ infectious units (20 µl) of the EIAV SIN-6.1CZW (HA/M2) vector (2×10$^8$ infectious units/ml) was instilled into the proximal tracheostomy (Estimated MOI=10). The vector dwell time was 2 hr. The animals were sacrificed 96 hr post-infection. Tracheas were removed and stained with X-Gal for histochemical analysis. 13A and 13B show en face views of X-Gal stained tracheas opened longitudinally. The control mouse was instilled with vehicle. All three mice transduced with the SIN-6.1CZW vector showed similar levels of X-Gal staining. 13C and 13D show histological sections counterstained with nuclear fast red. The airway lumen is to the top of the panel. All of the X-Gal staining was confined to the surface epithelium.

The mice were not subjected to treatments to injure or disrupt the integrity of the airway epithelium. Animals were sacrificed 96 hours after gene delivery and excised tracheas were stained for B-gal reporter gene expression with X-gal. It was found that significant transduction had occurred in the tracheas of animals inoculated with the HA pseudotyped EIAV SIN-6.1CZW vector (FIG. 13). The control mouse was instilled with vehicle. All three mice transduced with the SIN-6.1CZW vector showed similar levels of X-Gal staining. The airway lumen is to the top of the panel. All of the X-Gal staining was confined to the surface epithelium.

In a control experiment, 3-week-old mice in the control group (n=3) were exposed to air while mice in the $SO_2$ group (n=3) were exposed to 500 ppm $SO_2$ for three hours in inhalation chambers as previously described (Johnson et al. (1998) *J Virol* 72: 8861-72) to injure the airway epithelium in order to expose the basolaterally located receptors for the VSV-G envelope.

Double tracheotomies were performed on anesthetized mice within 30-60 minutes following $SO_2$ exposure. $8 \times 10^7$ infectious units (20 μl) of the VSV-G pseudotyped EIAV lacZ vector ($4 \times 10^9$ infectious units/ml) was instilled into the proximal tracheostomy of all six mice (Estimated MOI=10). This dose is 20 fold higher than that used with HA pseudotyped EIAV as described above. The vector dwell time was 2 hr. The animals were sacrificed 96 hr post-infection. Tracheas were removed and stained with X-Gal for histochemical analysis.

Figure 14:
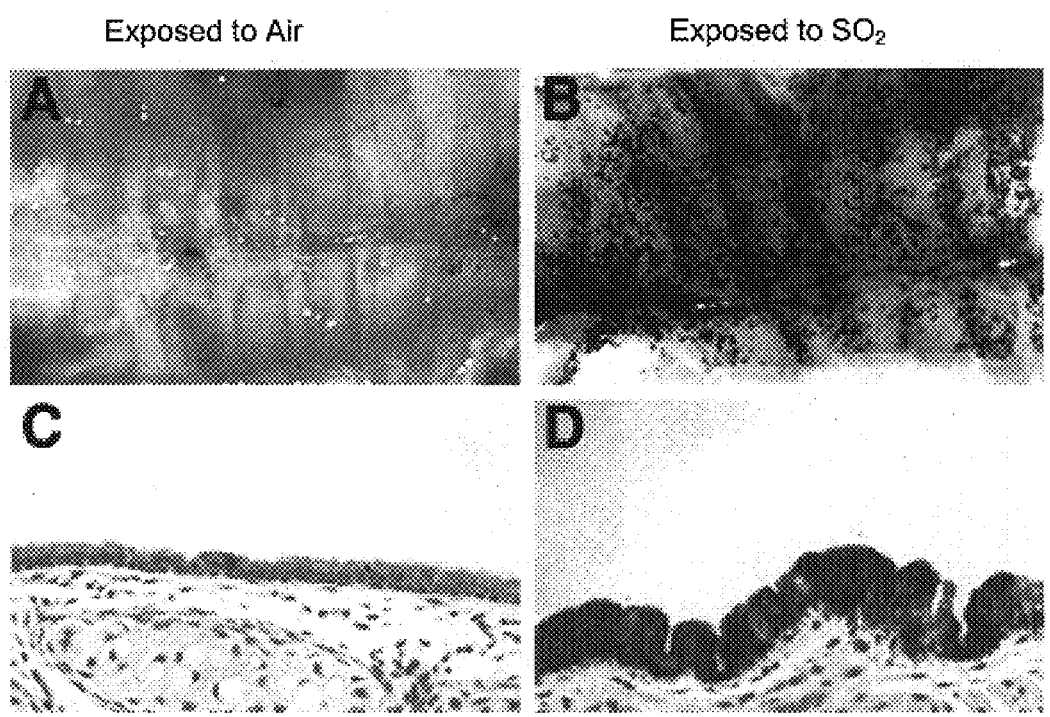
FIGS. 14A-14D show gene transfer to mouse trachea by VSV-G pseudotyped EIAV vector requires injury. 3-week-old mice in the control group (n=3) were exposed to air while mice in the SO$_2$ group (n=3) were exposed to 500 ppm SO$_2$ for three hours in inhalation chambers as previously described (Johnson et al. (1998) *J Virol* 72: 8861-72). Double tracheotomies were performed on anesthetized mice within 30-60 minutes following SO$_2$ exposure. 8×10$^7$ infectious units (20 µl) of the VSV-G pseudotyped EIAV lacZ vector (4×10$^9$ infectious units/ml) was instilled into the proximal tracheostomy of all six mice (Estimated MOI=10). The vector dwell time was 2 hr. The animals were sacrificed 96 hr post-infection. Tracheas were removed and stained with X-Gal for histochemical analysis. 14A and 14B show en face views of X-Gal stained tracheas opened longitudinally. All three mice in each group showed similar levels of X-Gal staining. 14C and 14D show histologic sections counterstained with nuclear fast red. The airway lumen is at the top of the panel. All of the X-Gal staining was confined to the surface epithelium.

With VSV-G pseudotyping very little gene delivery occurred to the airway epithelium in the absence of injury, however, significant gene delivery was achieved in animals exposed to $SO_2$ gas (FIG. 14).

Figure 15:
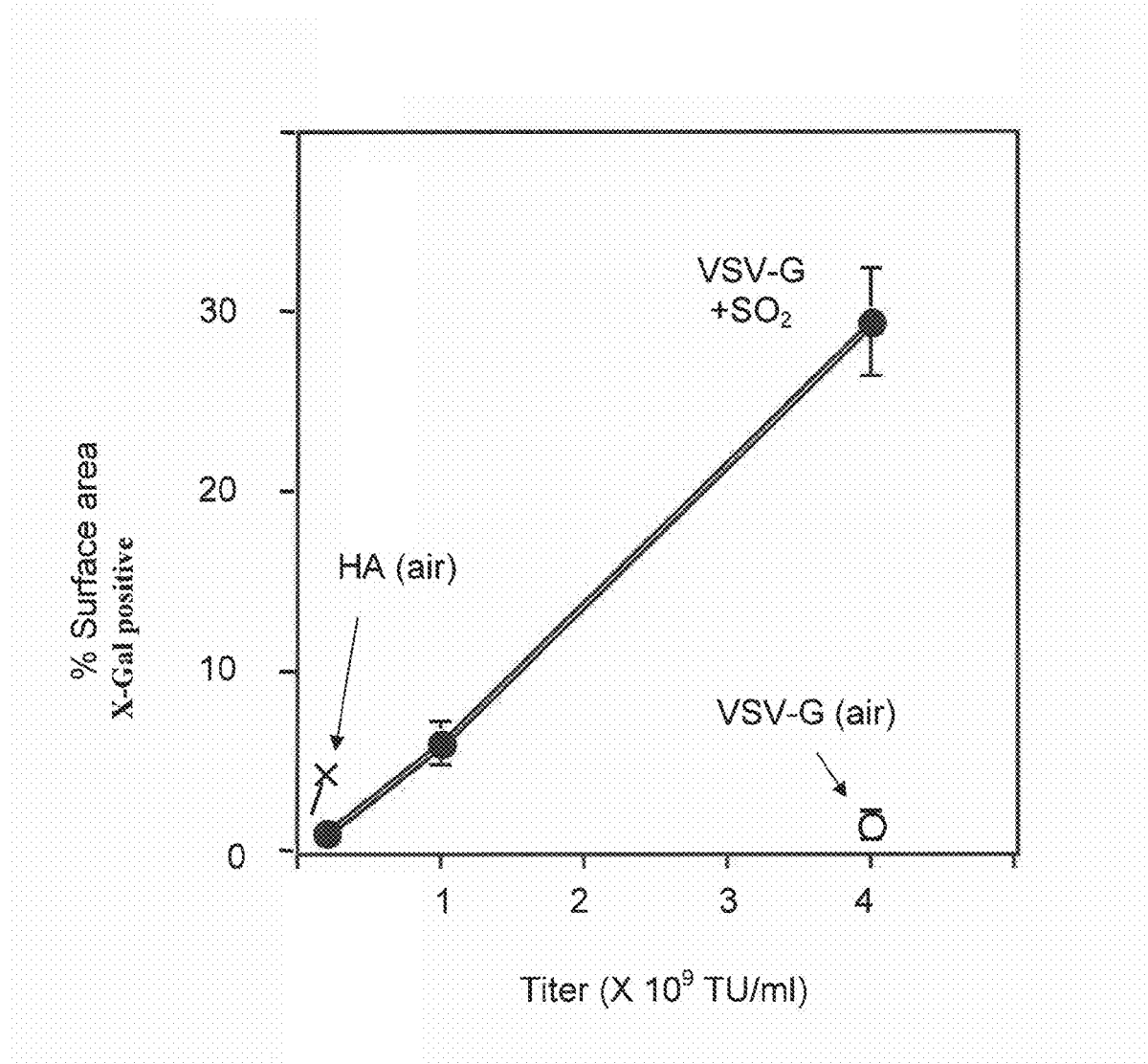

The dose response data of the in vivo gene delivery is summarized in FIG. 15. The HA pseudotyped virus is much more efficient at delivering genes at low doses to the trachea than VSV-G pseudotyped virus.

The % surface area X-Gal positive was estimated by measuring the area of cells staining X-gal positive compared to the total area of the trachea exposed to the vector using the Metamorph image analysis system.

These results demonstrate significant gene transfer and expression in surface epithelial cells can be achieved using HA pseudotyped EIAV even though the animals were not injured or otherwise treated to disrupt the integrity of the airway epithelium. These results suggest that hybrid influenza/lentiviral vectors may be useful tools for gene transfer to airway epithelia.

Example 12

Pseudotyping Studies

Figure 16:
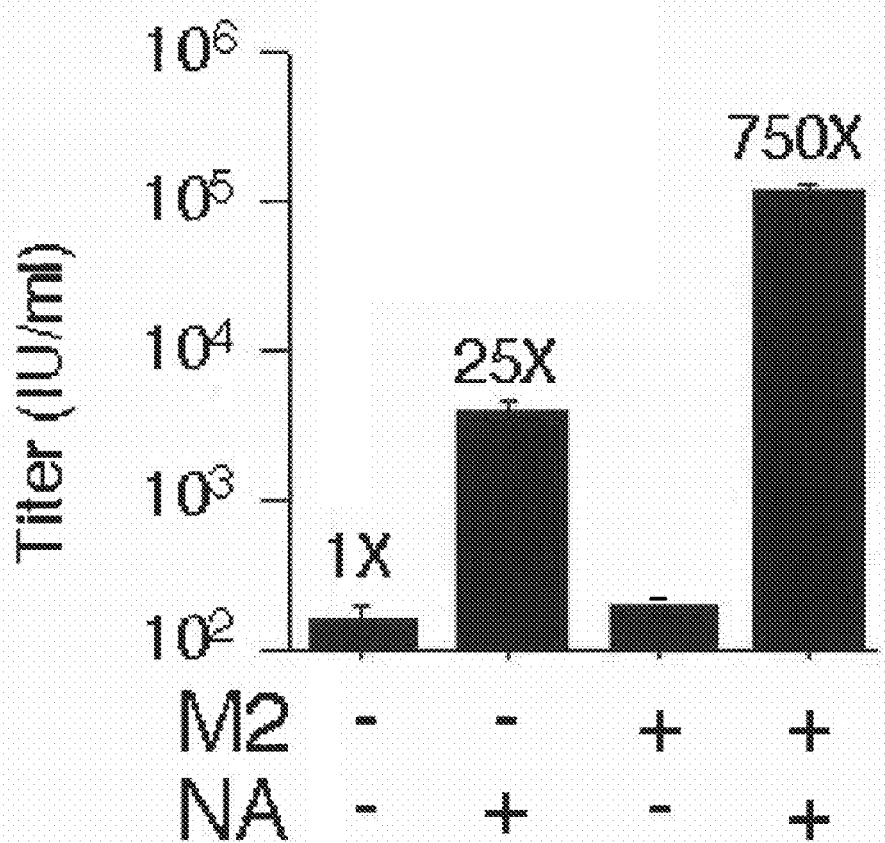
FIG. 16 shows the effect of expressing influenza NA and M2 on titers of EIAV vectors pseudotyped with HA. Titers were determined in 293T cells.
Figure 17:
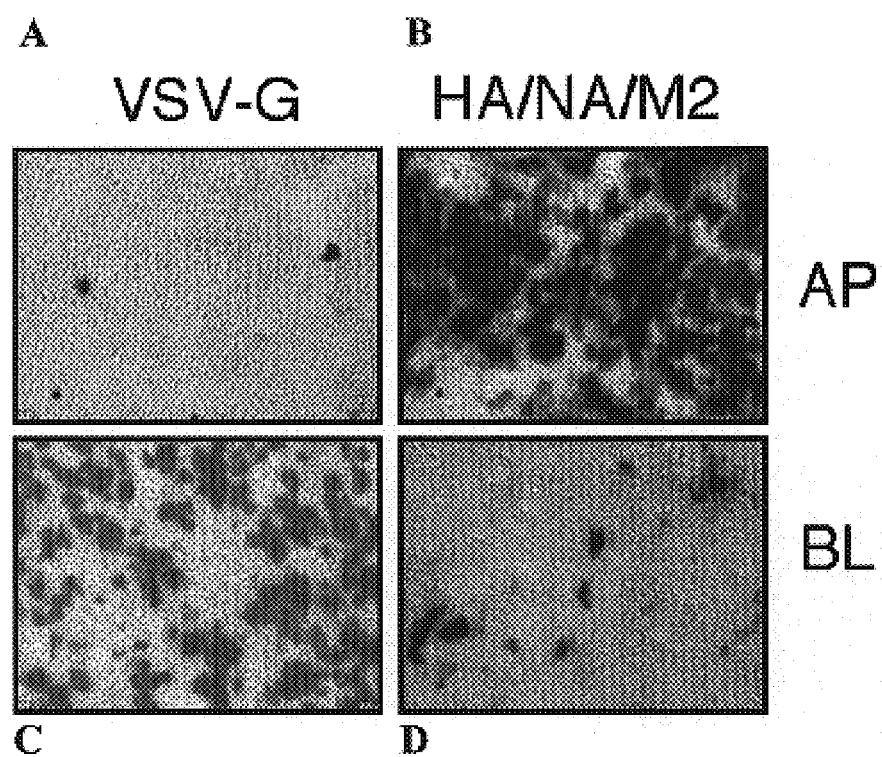
FIGS. 17A-17D show polarity of *lentivirus* gene transfer to MDCK cells by VSV-G and avian influenza virus HA/NA/M2 pseudotyped vectors. En face view of X-Gal stained cultures. AP, EIAV-lacZ vectors applied to apical membrane surface. BL, the filter inserts were turned upside down and the vectors applied to the basolateral membrane surface. The multiplicity of infection for each viral vector was 10 infectious units/cell. Cells were stained for X-Gal 96 hr after transduction.

We have optimized conditions for pseudotyping lentiviral vectors with hemagglutinin (HA) from the Rostock strain of fowl plague virus (FPV). It was found that expressing both the FPV M2 ion channel envelope protein and influenza neuraminidase (NA) envelope protein in producer cells synergized in increasing vector titers (FIG. 16). Expression of NA alone led to a 30-fold increase in vector titers while expressing both NA and M2 led to a 750-fold increase in titers, such that we now can routinely obtain HA pseudotyped lentiviral vectors (HA or M2) in excess of $10^5$ IU/ml. The advantage of HA pseudotyping compared to pseudotypng with VSV-G is that influenza sialic acid receptors are often on the apical membrane of polarized epithelia compared to the often basolateral location of VSV-G receptors. An example in this tropism difference is shown in FIG. 17. In this experiment, EIAV-lacZ vectors pseudotyped with VSV-G or FPV HA/NA/M2 were applied either to the apical or basolateral membranes of polarized (resistence>800 ohm-cm 2) MDCK cells grown on permeable transwell membrane supports (0.4 μM pore size). It was found that VSV-G pseudotyped vectors prefer exposure to the basolateral surface while HA pseudotyped vectors prefer exposure to the apical surface which are enriched in sialic acid residues.

Figure 18:
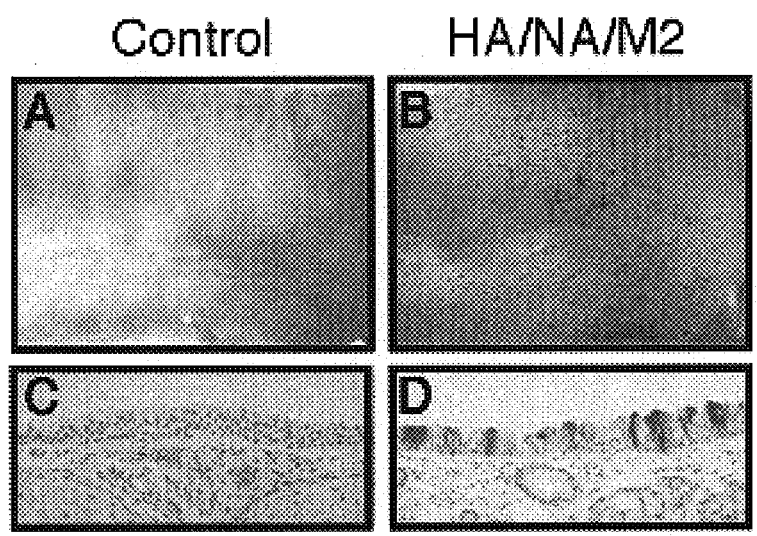
FIGS. 18A-18D show gene transfer to mouse trachea with HA pseudotyped EIAV-lacZ vector. 18A and 18B show en face views of X-Gal stained mouse tracheas 96 hr after gene transfer. 18C and 18D show sections of X-Gal stained tracheas. The X-Gal staining in 18D was confined to the surface epithelium.

Direct in vivo delivery showed that it was possible to use HA/NA/M2 pseudotyped EIAV-lacZ vectors to the trachea of mice without having to use methods to open up tight-junctions which is a requirement of VSV-G pseudotyping (Johnson et al., 1998, *J Virol* 72: 8861-72; Wang et al., 1999, *J Clin Invest* 104: R55-62; Johnson et al., 2000, *Gene Ther* 7: 568-74). In the experiment shown in FIG. 18, a HA/NA/M2 pseudotyped EIAV-lacZ vector was concentrated to a titer of $2 \times 10^8$ IU/ml by centrifugation and 20 μl was instilled into the tracheas of 3-week old mice using the double tracheostomy technique described previously (Johnson et al., 1998). We found that significant transduction was evident in the tracheas of all four mice harvested 4 days after gene transfer using the HA pseudotyping strategy. An example of one of the tracheas is shown in FIG. 18. In contrast, delivery of 20 μl VSV-G pseudotyped EIAV lacZ vector at a titer of $4 \times 10^9$ IU/ml resulted in lacZ staining no different than sham-infect controls. These results provide the premise for developing vectors using sialic acid receptors for airway delivery which may overcome rate limiting steps in vector entry.

Gene Transfer To Polarized Human Airway Epithelia

Our studies with the fowl plague virus (FPV) viral envelope proteins were helpful for studying the requirements of HA pseudotyping. This viral envelope may be useful for some gene transfer applications. For example, an FPV HA-pseudotyped vector was shown to efficiently transduce rat retinal epithelium (Duisit et al., 2002, *Mol Ther* 6: 446-54). However, it was unclear from the literature whether the FPV envelope could be used for transferring genes to human airways. In recent years avian influenza virus strains ($H_5N1$ and $H_7N_7$) have been shown to transmit from birds directly to humans without going through an intermediate animal reservoir. Humans infected with these viruses have symptoms of respiratory infection. However, the rarity of avian to human transmission may suggest some unknown special circumstances contributing to infection in these cases. On the other hand, a recent report showed that a chicken egg-adapted human influenza virus with the same sialic acid sugar specificity as FPV (α-2,3-linkage to galactose) could infect cultures of well-differentiated human epithelium (Slepushkin et al., 2001, *Mol Ther* 3: 395-402). In birds, FPV infection is primarily restricted to endothelial cells although many organs can be infected (Feldmann et al., 2000, *J Virol* 74: 8018-27). In studies described below we tested HA pseudotyping to well-differentiated human epithelium using the conditions we optimized for FPV envelope proteins.

Model For Well-Differentiated Human Airway Epithelia

Figure 19:
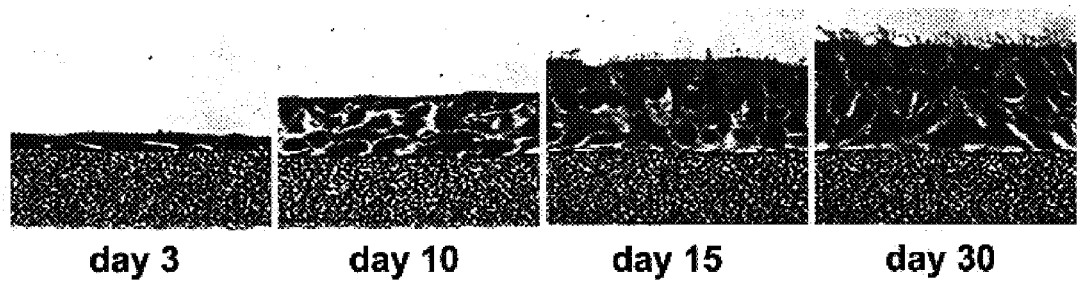
FIG. 19 shows differentiation of human airway epithelial cells on tissue culture inserts. Primary cultures, grown at an air/liquid interface on porous collagen membranes, were fixed on various days and processed for histology. Early in culture the cells are poorly differentiated. By day 15 ciliated cells are observed and by day 30 ciliated cells are numerous. Sections were stained with hematoxylin and eosin.

Our studies use primary or early passage human bronchial epithelial cells obtained from excess surgical tissue. These cells will be obtained from the UNC Cystic Fibrosis Cell Culture and Tissue Core (Dr. Scott Randell, director). Typically, 250,000 cells are plated out on 12 mm diameter collagen-coated tissue culture supports (Transwell-col). Cultures are maintained in well-defined growth media and after reaching confluence (2-3 days) medium is removed form the apical compartment and cells are fed only from the basal compartment. Cells cultured under these conditions differentiate into a mucociliary epithelium that shares many properties of the intact tracheobronchial epithelium. These cultures undergo ciliogenesis (FIG. 19) and have been used previously as a model for gene transfer to human cells, e.g. Pickles et al., 1998, *J Virol* 72: 6014-23; Johnson et al., 2000.

Figure 20:
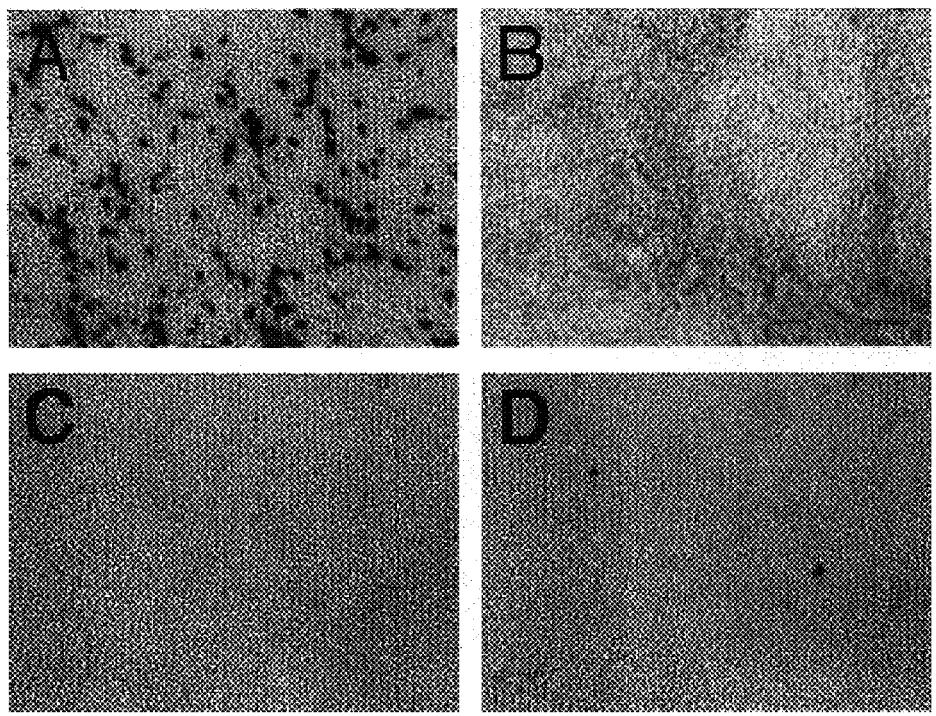
FIGS. 20A-20D show gene transfer to human airway epithelial cells grown on collagen coated supports. 20A shows 10 day culture infected with EIAV-lacZ (HA pseudotyped). 20B shows 30 day culture infected with EIAV-lacZ (HA). 20C shows mock infected 10 day culture. 20D shows EIAV-lacZ (VSV-G pseudotyped) 10 day cultures. Cultures were infected with 50 µl virus at a titer of 2×10$^7$ IU/ml. Cultures were stained 96 hr after gene transfer.

Gene Transfer to Well-Differentiated Epithelia Using Vectors Pseudotyped with Fowl Plague Virus HA To determine if FPV HA pseudotyped EIAV lentiviruses could transfer genes to human airway epithelial cells cultured using the above model, EIAV-lacZ lentiviral vectors were applied to the apical membrane surface on day 10 or day 30 cultures. We found that poorly differentiated (PD) day 10 cultures were good hosts for transduction (FIG. 20A) but well-differentiated (WID) 30 day cultures were not transduced (FIG. 20B). We also found that HA pseudotyped vectors were more efficient than VSV-G pseudotyped vectors at infecting day 10 cultures (Compare FIGS. 20A and 20D).

Inactivation of FPV HA Pseudotyped Viruses by Airway Surface Liquid

Figure 21:
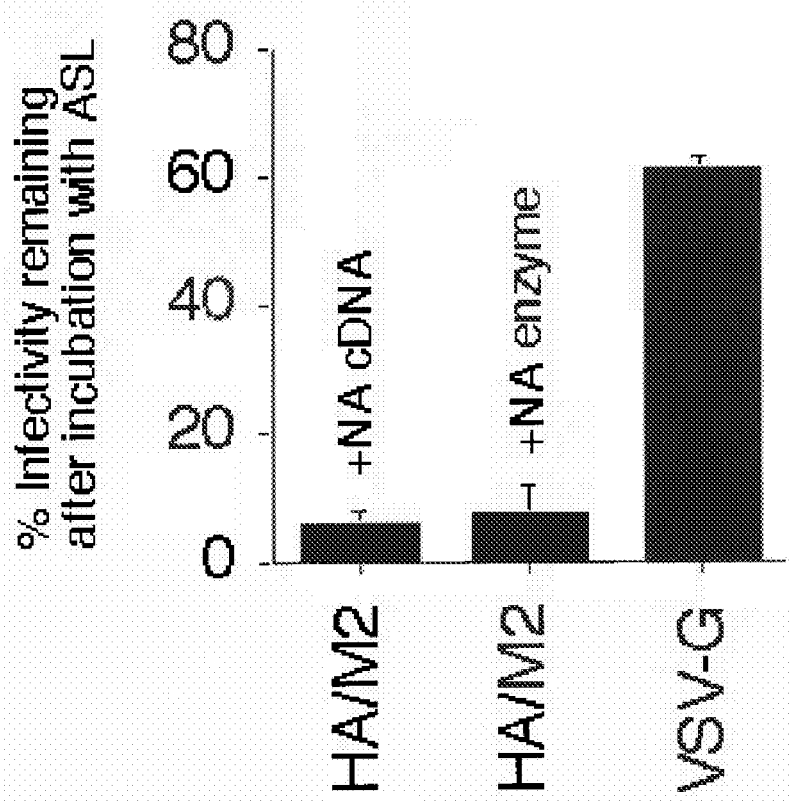
FIG. 21 shows loss of infectivity of FPV HA pseudotyped EIAV-lacZ vector incubated with surface liquid from WD cultures.

The airway surface liquid (ASL) of well-differentiated cultures is known to contain mucins and other components that could act as barriers to gene transfer. To test this, we removed the mucus layer from the airway surface liquid of the apical membrane compartment from 28-day WD cultures. This was mixed 1:1 with EIAV-lacZ vectors pseudotyped with VSV-G or FPV HA and incubated for 10 minutes at room temperature prior to transduction of 293T cells. For this experiment, FPV HA pseudotyped virus was prepared using either NA cDNA or bacterial neuraminidase to see if there were differences. It was found that pre-incubating the FPV HA pseudotype with ASL resulted in loss of infectivity (FIG. 21). In contrast, the VSV-G pseudotyped virus was significantly more resistant to exposure to the mucous layer. Also, the method of preparing the FPV HA pseudotyped vector made no difference in preserving infectivity.

Infection of Well-Differentiated Cultures by Human Influenza Virus

Figure 22:
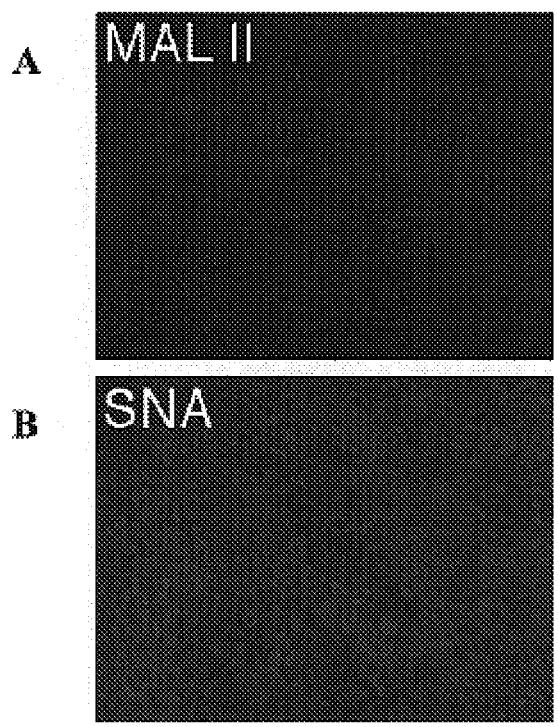
FIGS. 22A and 22B show an en face view of Lectin binding to cultures of human well-differentiated airway epithelia.
Figure 23:
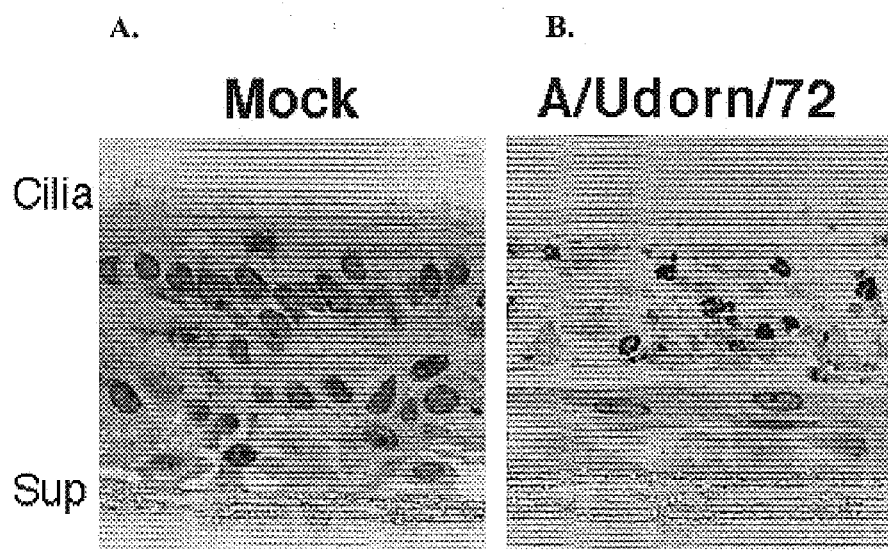
FIGS. 23A and 23B show A/Udorn/72 infection of cultured human well differentiated airway epithelia. At hr post-infection (MOI=0.1), cultures were fixed and sectioned. Sections were stained with hematoxylin/eosin. The apical surface is at the top. Sup, collagen-coated filter support.

Influenza viruses differ in their receptor specificity. Avian influenza viruses generally prefer neuraminic acid bound by α-2,3-linkage to galactose, (NeuAc-α-2,3-Gal) whereas human influenza viruses prefer α-2,6-linkage to galactose. To determine the expression of neuraminic acid in well-differentiated cells, we determined the lectin binding specificity to WD cells using MAL II, specific for NeuAc-α-2,3-Gal, and SNA, specific for NeuAc-α-2,6-Gal. The results shown in FIG. 22 indicate that (NeuAc-α-2,6-Gal) is very abundant on these cultures while NeuAc-α-2,3-Gal is not. It should be noted that these lectins react to protein-bound oligosaccharides and not with gangliosides. It is not clear if glycolipids can serve as receptors in these cells. Nonetheless, the significant concentration of NeuAc-α-2,6-Gal on the apical surface of these cells has prompted us to investigate the infectivity of WD cultures by human influenza A viruses. In the experiment shown in FIG. 23, cultures were infected with A/Udorn/72 virus ($H_3N_2$) at an multiplicity of infection of 0.1 infectious unit per cell. By 18 hours post-infection, the cultures demonstrated evidence of severe cytopathology. Significant cell detachment had occurred and evidence of ciliary activity had also decreased. Histologic sections confirmed the loss of cilia and loss of cells (FIG. 23). In other experiments, we found a similar cytopathic effect after infection of WD cells with A/Aichi/2/68 but not with A/PR/8/34 which prefers NeuAc-α-2,3-Gal receptors (Slepushkin et al., 2001). Previously, it was reported that WD cultures are capable of producing A/PR/Rico/8/34, however, titers were low compared to production by MDCK cells (Slepushkin et al., 2001).

Efficient Gene Transfer to Well-Differentiated Mouse Tracheal Cultures

Figure 24:
FIG. 24 shows cultured mouse tracheal epithelial cells. Histologic section stained with H&E obtained 25 days after air-liquid interface culture on collagen-coated supports. (Figure courtesy of Dr. S. Randell, UNC Molecular Therapy Core Center).

HA pseudotyped EIAV gene transfer to cultured human airway epithelia was inefficient while gene transfer to mouse trachea in vivo was promising. To investigate this further we decided to investigate gene transfer to cultured mouse airway. Recently, an in vitro culture model system of differentiated mouse tracheal airway epithelium (MTE) was described (You et al., 2003, *Am J Physiol Lung Cell Mol Physiol*). Fully differentiated cultures exhibit morphology similar to that in vivo, with 30% or more of the cells on the apical surface containing cilia (FIG. 24). Furthermore, these cultures exhibit other characteristics of a mature epithelium including formation of tight junctions with transmembrane resistances >1000 ohm-cm 2. At UNC, mouse tracheal cultures are now readily available to us (free of charge as of Apr. 1, 2004) from the Molecular Therapy Core Center directed by Dr. Scott H. Randell.

Figure 25:
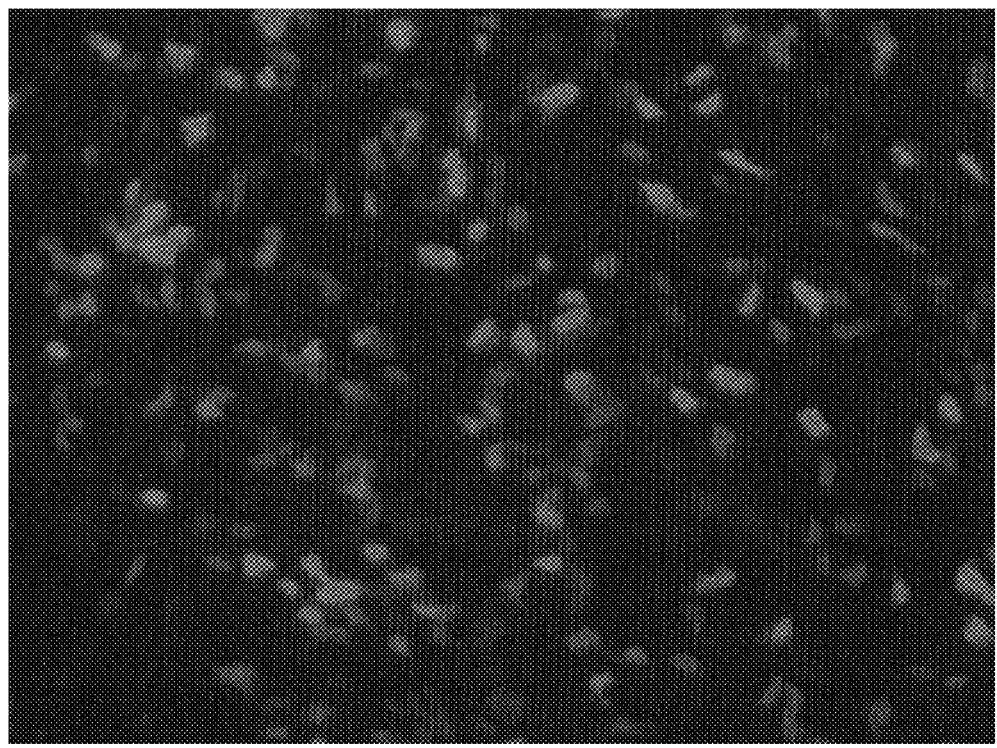
FIG. 25 shows gene transfer to differentiated mouse tracheal epithelial (MTE) cells. An EIAV EGFP vector pseudotyped with FPV HA was applied to the apical surface of 30-day MTE cultures. This fluorescent en face view was captured 5 days after gene transfer.
Figure 26:
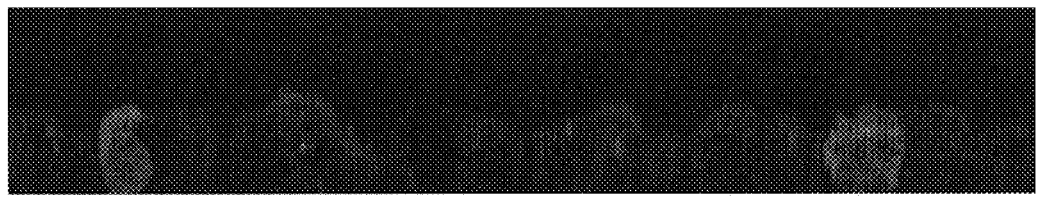
FIG. 26 shows gene transfer to differentiated MTE cultures. An EIAV EGFP vector was applied to the apical surface of well-differentiated MTE cultures as in FIG. 25. Five days after gene transfer the culture was fixed, embedded in paraffin and sectioned. De-paraffinized sections were doubly-stained with antibodies specific for EGFP (green) and beta-tubulin (identifies ciliated cells, red). The apical surface is at the top of the figure. The transduced cell on the left is non-ciliated. The transduced cell to the right is a ciliated cell.

To test lentiviral-mediated gene transfer to differentiated MTE cultures, an EIAV vector containing an EGFP reporter gene was pseudotyped with HA from fowl plague virus (FPV). This vector was delivered (estimated MOI=3-5) to the apical membrane of 30-day MTE cultures cultured at an air-liquid interface. It was found that these cultures, in contrast to human cultures, could be efficiently transduced with FPV HA pseudotyped EIAV vector (FIG. 25). Currently, we are characterizing cell types (ciliated, non-ciliated) that express EGFP (FIG. 26). It should be noted that one difference between the mouse and human airway culture systems is that MTE cultures secrete considerably less mucous than the human cultures, although studies by You et al. (2003) have shown that mucous is present attached to the apical surface of mature cells. The presence of mucins tethered to the apical surface of these cultures has been confirmed.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

I claim:

1. A retroviral vector production system for producing a retroviral vector pseudotyped with influenza HA and M2 that is capable of transducing an airway epithelial target site, comprising a first nucleotide sequence encoding an influenza HA protein capable of recognizing the target site; a second nucleotide sequence encoding an influenza M2 protein; and a retroviral vector nucleotide sequence that can be expressed and assembled into a pseudotyped retroviral particle.

2. The retroviral vector production system according to claim 1, wherein the retroviral vector is a lentiviral vector.

3. The retroviral vector production system according to claim 1, wherein the retroviral vector is an EIAV, HIV, FIV or MLV retroviral vector.

4. The retroviral vector production system according to claim 1, wherein the retroviral vector production system comprises at least one nucleotide sequence of interest (NOI).

5. The retroviral vector production system according to claim 4, wherein the NOI has a therapeutic effect or codes for a protein that has a therapeutic effect.

6. The retroviral vector production system according to claim 1, wherein the target site is a polarised airway epithelial cell.

7. The retroviral vector production system according to claim 1, wherein the target site is a human airway epithelial cell.

8. The retroviral vector production system according to claim 1, further comprising a third nucleotide sequence encoding an influenza neuraminidase (NA) protein.

9. A retroviral vector pseudotyped with influenza HA and M2, wherein the retroviral vector comprises an NOI, and wherein the NOI is capable of being expressed in an airway epithelial target cell transduced by the retroviral vector.

10. A composition comprising the retroviral vector according to claim 9, and an acceptable carrier.

11. A method for transducing an airway epithelial cell comprising contacting the cell with the retroviral vector according to claim 9.

12. A plurality of expression vectors for preparing the retroviral vector production system according to claim 1, comprising an expression vector that comprises a nucleotide sequence encoding influenza HA protein and a nucleotide sequence encoding influenza M2 protein, wherein the HA and M2 proteins are FPV HA and M2 proteins, and at least one other expression vector that comprises one or more retroviral nucleotide sequences necessary for the production of the retroviral vector pseudotyped with influenza HA and M2.

13. A method of pseudotyping a retrovirus with an influenza HA protein and M2 protein comprising contacting a producer cell with the retroviral vector production system of claim 1, thereby pseudotyping the retrovirus with the influenza HA protein and M2 protein.

14. A retroviral vector pseudotyped with influenza HA, M2 and NA, wherein the retroviral vector comprises an NOI, and wherein the NOI is capable of being expressed in an airway epithelial target cell transduced by the retroviral vector.

15. A composition comprising the retroviral vector according to claim 14, and an acceptable carrier.

16. A method for transducing an airway epithelial cell comprising contacting the cell with the retroviral vector according to claim 14.

17. The retroviral vector production system of claim 1, wherein the HA and M2 proteins are FPV HA and M2 proteins.

18. The retroviral vector production system of claim 8, wherein the retroviral vector is a lentiviral vector.

19. The retroviral vector production system of claim 8, wherein the retroviral vector is an EIAV, HIV, FIV or MLV retroviral vector.

20. The retroviral vector production system of claim 8, wherein the retroviral vector comprises at least one NOI.

21. The retroviral vector production system of claim 20, wherein the NOI has a therapeutic effect or codes for a protein that has a therapeutic effect.

22. The retroviral vector production system of claim 8, wherein the target site is a polarised airway epithelial cell.

23. The retroviral vector production system of claim 8, wherein the target site is a human airway epithelial cell.

24. A plurality of expression vectors for preparing the retroviral vector production system according to claim 8, comprising an expression vector that comprises a nucleotide sequence encoding influenza HA protein and a nucleotide sequence encoding influenza M2 protein, and a nucleotide sequence encoding influenza NA protein, wherein the HA and M2 proteins are FPV HA and M2 proteins, and at least one other expression vector comprises one or more retroviral nucleotide sequences necessary for the production of the retroviral vector pseudotyped with influenza HA, M2 and NA.

25. A method of pseudotyping a retrovirus with an influenza HA protein, M2 protein, and NA protein comprising contacting the retroviral vector production system of claim 8, thereby pseudotyping the retrovirus with the influenza HA protein, M2 protein, and NA protein.

* * * * *

UNITED STATES PATENT AND TRADEMARK OFFICE
CERTIFICATE OF CORRECTION

PATENT NO. : 7,659,113 B2
APPLICATION NO. : 10/910845
DATED : February 9, 2010
INVENTOR(S) : John Christian Olsen It is certified that error appears in the above-identified patent and that said Letters Patent is hereby corrected as shown below:

Column 1, lines 14-15, should read:

"This work may have been supported in part by National Institutes of Health Grant HL051818."

-- This invention was made with government support under Grant HL051818 awarded by National Institutes of Health. The government has certain rights in the invention. --

Signed and Sealed this

Thirteenth Day of April, 2010

David J. Kappos
*Director of the United States Patent and Trademark Office*

```
                        SEQUENCE LISTING

<160> NUMBER OF SEQ ID NOS: 1

<210> SEQ ID NO 1
<211> LENGTH: 563
<212> TYPE: PRT
<213> ORGANISM: Influenza A virus

<400> SEQUENCE: 1

Met Asn Thr Gln Ile Leu Val Phe Ala Leu Val Ala Val Ile Pro Thr
  1               5                  10                  15

Asn Ala Asp Lys Ile Cys Leu Gly His His Ala Val Ser Asn Gly Thr
             20                  25                  30

Lys Val Asn Thr Leu Thr Glu Arg Gly Val Glu Val Val Asn Ala Thr
         35                  40                  45

Glu Thr Val Glu Arg Thr Asn Ile Pro Lys Ile Cys Ser Lys Gly Lys
     50                  55                  60

Arg Thr Thr Asp Leu Gly Gln Cys Gly Leu Leu Gly Thr Ile Thr Gly
 65                  70                  75                  80

Pro Pro Gln Cys Asp Gln Phe Leu Glu Phe Ser Ala Asp Leu Ile Ile
                 85                  90                  95

Glu Arg Arg Glu Gly Asn Asp Val Cys Tyr Pro Gly Lys Phe Val Asn
            100                 105                 110

Glu Glu Ala Leu Arg Gln Ile Leu Arg Gly Ser Gly Gly Ile Asp Lys
        115                 120                 125

Glu Thr Met Gly Phe Thr Tyr Ser Gly Ile Arg Thr Asn Gly Thr Thr
    130                 135                 140

Ser Ala Cys Arg Arg Ser Gly Ser Ser Phe Tyr Ala Glu Met Glu Trp
145                 150                 155                 160

Leu Leu Ser Asn Thr Asp Asn Ala Ser Phe Pro Gln Met Thr Lys Ser
```

-continued

```
                165                 170                 175
Tyr Lys Asn Thr Arg Arg Glu Ser Ala Leu Ile Val Trp Gly Ile His
            180                 185                 190
His Ser Gly Ser Thr Thr Glu Gln Thr Lys Leu Tyr Gly Ser Gly Asn
            195                 200                 205
Lys Leu Ile Thr Val Gly Ser Ser Lys Tyr His Gln Ser Phe Val Pro
            210                 215                 220
Ser Pro Gly Thr Arg Pro Gln Ile Asn Gly Gln Ser Gly Arg Ile Asp
225                 230                 235                 240
Phe His Trp Leu Ile Leu Asp Pro Asn Asp Thr Val Thr Phe Ser Phe
                245                 250                 255
Asn Gly Ala Phe Ile Ala Pro Asn Arg Ala Ser Phe Leu Arg Gly Lys
            260                 265                 270
Ser Met Gly Ile Gln Ser Asp Val Gln Val Asp Ala Asn Cys Glu Gly
            275                 280                 285
Glu Cys Tyr His Ser Gly Gly Thr Ile Thr Ser Arg Leu Pro Phe Gln
            290                 295                 300
Asn Ile Asn Ser Arg Ala Val Gly Lys Cys Pro Arg Tyr Val Lys Gln
305                 310                 315                 320
Glu Ser Leu Leu Leu Ala Thr Gly Met Lys Asn Val Pro Glu Pro Ser
                325                 330                 335
Lys Lys Arg Glu Lys Arg Gly Leu Phe Gly Ala Ile Ala Gly Phe Ile
            340                 345                 350
Glu Asn Gly Trp Glu Gly Leu Val Asp Gly Trp Tyr Gly Phe Arg His
            355                 360                 365
Gln Asn Ala Gln Gly Glu Gly Thr Ala Ala Asp Tyr Lys Ser Thr Gln
            370                 375                 380
Ser Ala Ile Asp Gln Ile Thr Gly Lys Leu Asn Arg Leu Ile Glu Lys
385                 390                 395                 400
Thr Asn Gln Gln Phe Glu Leu Ile Asp Asn Glu Phe Thr Glu Val Glu
                405                 410                 415
Lys Gln Ile Gly Asn Leu Ile Asn Trp Thr Lys Asp Phe Ile Thr Glu
            420                 425                 430
Val Trp Ser Tyr Asn Ala Glu Leu Leu Val Ala Met Glu Asn Gln His
            435                 440                 445
Thr Ile Asp Leu Ala Asp Ser Glu Met Asn Lys Leu Tyr Glu Arg Val
450                 455                 460
Arg Lys Gln Leu Arg Glu Asn Ala Glu Glu Asp Gly Thr Gly Cys Phe
465                 470                 475                 480
Glu Ile Phe His Lys Cys Asp Asp Cys Met Ala Ser Ile Arg Asn
            485                 490                 495
Asn Thr Tyr Asp His Ser Lys Tyr Arg Glu Glu Ala Met Gln Asn Arg
            500                 505                 510
Ile Gln Ile Asp Pro Val Lys Leu Ser Ser Gly Tyr Lys Asp Val Ile
            515                 520                 525
Leu Trp Phe Ser Phe Gly Ala Ser Cys Phe Leu Leu Ala Ile Ala
            530                 535                 540
Val Gly Leu Val Phe Ile Cys Val Lys Asn Gly Asn Met Arg Cys Thr
545                 550                 555                 560
Ile Cys Ile
```